United States Patent
Elzein et al.

(10) Patent No.: US 7,381,714 B2
(45) Date of Patent: Jun. 3, 2008

(54) A1 ADENOSINE RECEPTOR AGONISTS

(75) Inventors: Elfatih Elzein, Fremont, CA (US); Rao Kalla, Sunnyvale, CA (US); Thao Perry, San Jose, CA (US); Jeff Zablocki, Mountain View, CA (US); Xiaofen Li, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 8 days.

(21) Appl. No.: 11/437,774

(22) Filed: May 19, 2006

(65) Prior Publication Data

US 2006/0276428 A1 Dec. 7, 2006

Related U.S. Application Data

(60) Provisional application No. 60/683,263, filed on May 19, 2005.

(51) Int. Cl.
*A61K 31/70* (2006.01)
*C07H 19/167* (2006.01)

(52) U.S. Cl. .................. 514/46; 536/27.22; 536/27.23; 536/27.61

(58) Field of Classification Search ...................... None
See application file for complete search history.

(56) References Cited

U.S. PATENT DOCUMENTS

| 5,789,416 | A | 8/1998 | Lum et al. |
| 6,514,949 | B1 * | 2/2003 | Linden et al. ................. 514/46 |
| 6,642,210 | B1 | 11/2003 | Zablocki et al. |
| 2004/0116376 | A1 | 6/2004 | Elzein et al. |

FOREIGN PATENT DOCUMENTS

WO WO 01/37845 A 5/2001

OTHER PUBLICATIONS

Pagonopoulou et al., "Modulatory Role of Adenosine and Its Receptors in Epilepsy: Possible Therapeutic Approaches," Neuroscience Research, 56(1), 14-20 (Sep. 2006).*
De Sarro et al., "Effects of Adenosine Receptor Agonists and Antagonists on Audiogenic Seizure-Sensible DBA/2 Mice," European Journal of Pharmacology, 371(2-3), 137-145 (Apr. 28, 1999).*
Kashiwagi et al., "Rationale and Hurdles of Inhibitors of Hepatic Gluconeogenesis in Treatment of DIabetes Mellitus," Diabetes Research and Clinical Practice, 28(Supp.), S195-S200 (Aug. 1995).*
Németh et al., "Adenosine Receptor Activation Ameliorates Type 1 Diabetes," FASEB Journal, 21(10), 2379-2388 (Aug. 2007).*
Dhalla et al., "A1 Adenosine Receptor Partial Agonist Lowers Plasma FFA and Improves Insulin Resistance Induced by High-Fat Diet in Rodents," Am. J. of Physiology: Endocrinology & Metabolism, 292(5), E1358-1363 (May 2007).*
Dong et al., "Overexpression of the A1 Adenosine Receptor in Adipose Tissue Protects Mice from Obesity-Related Insulin Resistance," Diabetes, Obesity and Metabolism, 3(5), 360-366 (Oct. 2001).*
Van Schaick et al., "Metabolic and Cardiovascular Effects of the Adenosine A1 Receptor Agonist N6-(p-Sulfophenyl)Adenosine in Diabetic Zucker Rats: Influence of the Disease on the Selectivity of Action," J. Pharmacology & Experimental Therapeutics, 287(1), 21-30 (Oct. 1998).*
Donnelly et al., "Mechanisms of Insulin Resistance and New Pharmacoloigcal Approaches to Metabolism and Diabetic Complications," Clinical & Experimental Pharmacology & Physiology, 25(2), 79-87 (Feb. 1998).*
Shah et al., "Pharmacokinetics, Pharmacodynamics, and Safety of a Lipid-Lowering Adenosine A1 Agonist, RPR749, in Health Subjects," American Journal of Therapeutics, 11(3), 175-189 (May-Jun. 2004).*
Van Der Graaf et al., "Mechanism-Based Pharmacokinetic-Pharmacodynamic Modeling of Antilipolytic Effects of Adenosine A1 Receptor Agonists in Rats: Prediction of Tissue-Dependent Efficacy In Vivo," J. Pharmacology & Experimental Therapeutics, 290(2), 702-709 (Aug. 1999).*
Elzein et al; "2-Pyrazolyl-N6-Substituted Adenosine Derivatives as High Affinity and Selective Adenosine A3 Receptor Agonists"; Jounal of Medicinal Chemistry, American Chemical Society. Washington, us, vol. 47, No. 19, Aug. 7, 2004, pp. 4766-4773.
Cosyn et al; "2-(1,2,3-triazol-1-yl) N6-CH#-Substituted Adenosine Derivatives: Highly Potent and Selective A3 Receptor Ligands"; Collection Symposium Series, 7(Chemistry of Nucleic Acid Components), pp. 393-394 CODEN: CSYSFN, 2005.

* cited by examiner

Primary Examiner—L. E. Crane
(74) Attorney, Agent, or Firm—J. Elin Hartrum; Michael J. Beck

(57) ABSTRACT

Disclosed are novel compounds that are partial and full $A_1$ adenosine receptor agonists having the structure of Formula I:

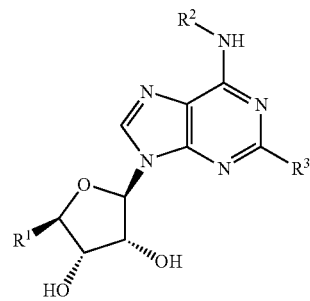

which are useful for treating various disease states, in particular tachycardia and atrial flutter, angina, and myocardial infarction.

22 Claims, No Drawings

A1 ADENOSINE RECEPTOR AGONISTS

CROSS REFERENCE TO RELATED APPLICATIONS

This application claims priority to U.S. Provisional Patent Application Ser. No. 60/683,263, filed May 19, 2005, the complete disclosure of which is hereby incorporated by reference.

FIELD OF THE INVENTION

The present invention relates to novel compounds that are partial or full $A_1$ adenosine receptor agonists, and to their use in treating mammals for various disease states, including modifying cardiac activity, in particular treatment of arrhythmia. The compounds are also useful for treating CNS disorders, diabetic disorders, obesity, and modifying adipocyte function. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, activation of the $A_{2A}$ adenosine receptors causes coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148-153), and $A_3$ adenosine receptors modulate cell proliferation processes.

The $A_1$ adenosine receptor is coupled to two distinct signaling pathways in heart cells. The first pathway is $A_1$ adenosine receptor to inhibitory $G_{oc}$ protein to inhibition of adenylate cyclase activity to attenuation of the cardiostimulatory effects of catecholamines. The second signaling pathway is $A_1$ adenosine receptor to inhibitory G protein βγ subunits to activation of $I_{kAdo}$ to slowing of both atrial SA nodal pacemaking and conduction of electrical impulses through the AV node. (B. Lerman and L. Belardinelli *Circulation*, Vol. 83 (1991), P 1499-1509 and J. C. Shryock and L. Belardinelli *The Am. J. Cardiology*, Vol. 79 (1997) P 2-10). Stimulation of the $A_1$ adenosine receptor shortens the duration and decreases the amplitude of the action potential of AV nodal cells, and hyperpolarizes and hence prolongs the refractory period of the AV nodal cell. Thus, stimulation of $A_1$ receptors provides a method of treating supraventricular tachycardias, including termination of nodal re-entrant tachycardias, and of controlling ventricular rate during atrial fibrillation and flutter.

Accordingly, $A_1$ adenosine receptor agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ adenosine receptor agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli *Circulation*, Vol. 83 (1991), P 1499-1509 and J. C. Shryock and L. Belardinelli, *Am. J. Cardiology*, Vol. 79 (1997) P 2-10.

$A_1$ adenosine receptor agonists, as a result of their inhibitory action on cyclic AMP generation, have anti-lipolytic effects in adipocytes that lead to a decreased release of non-esterified fatty acids (NEFA) (E. A. van Schaick et al J. Pharmacokinetics and Biopharmaceutics, Vol. 25 (1997) p 673-694 and P. Strong *Clinical Science* Vol. 84 (1993) p. 663-669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al *Metab. Clin. Exp.* Vol. 31 (1982)p 1128-1136 and G. Bodenetal *J. Clin. Invest.* Vol. 93 (1994)p 2438-2446). A glucose fatty acid cycle was proposed by P. J. Randle as early as 1963 (P. J. Randle et al (1963) *Lancet* p. 785-789). A tenet of this hypothesis would be that limiting the supply of fatty acids to the peripheral tissues should promote carbohydrate utilization (P. Strong et al *Clinical Science* Vol. 84 (1993) p. 663-669).

The benefit of $A_1$ adenosine receptor agonists in central nervous disorders has been reviewed (L. J. S. Knutsen and T. F. Murray In Purinergic Approaches in Experimental Therapeutics, Eds. K. A. Jacobson and M. F. Jarvis (1997) Wiley-Liss, N. Y., P-423-470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. *J. Pharmacol.* (1993) Vol. 224 p. 221-228). In other studies using CGS 21680, an $A_{2A}$ agonist, it was concluded that the anticonvulsant activity was attributed to activation of $A_1$ adenosine receptor agonists (G. Zhang et al. *Eur. J. Pharmacol.* Vol. 255 (1994) p. 239-243). Furthermore, $A_1$ adenosine receptor agonists have been shown to have anticonvulsant activity in the DMCM model (L. J. S. Knutsen, Adenosine and Adenine Nucleotides: From Molecular Biology to Integrative Physiology; eds. L. Belardinelli and A. Pelleg, Kluwer: Boston, 1995, pp 479-487). A second area where an $A_1$ adenosine agonist has a benefit is in animal models of forebrain ischemia as demonstrated by Knutsen et al (*J. Med. Chem.* Vol. 42 (1999) p. 3463-3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_1$, $A_{2A}$, $A_{2B}$, and the $A_3$ adenosine receptor subtypes, it also provides direct effects on sympathetic tone, coronary vasodilatation, systemic vasodilatation and mast cell degranulation.

Accordingly, it is an object of this invention to provide compounds that are potent full $A_1$ adenosine receptor agonists or partial $A_1$ receptor agonists with a half life greater than that of adenosine, and that are selective for the $A_1$ adenosine receptor, which will ensure that undesired side effects related to stimulation or antagonism of the other adenosine receptors are avoided.

SUMMARY OF THE INVENTION

It is an object of this invention to provide a method of treating a disease or condition that can be treated with partial or full selective $A_1$ adenosine receptor agonists using a compound having the structure of Formula I:

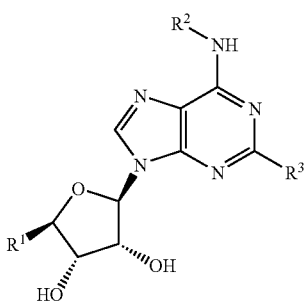

wherein:

$R^1$ is hydroxymethyl, —C(O)OR$^6$, or —C(O)NHR$^6$, in which $R^6$ is hydrogen, optionally substituted alkyl, optionally substituted cycloalkyl, optionally substituted aralkyl, optionally substituted aryl, or optionally substituted heteroaryl;

$R^2$ is optionally substituted alkyl, optionally substituted cycloalkyl, optionally substituted heterocyclyl, optionally substituted aryl, or optionally substituted heteroaryl; and $R^3$ is selected from

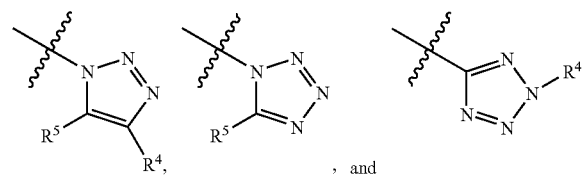

wherein $R^4$ and $R^5$ are independently chosen from hydrogen, optionally substituted alkyl, optionally substituted aryl, optionally substituted heteroaryl, —CO$_2$H, —SO$_3$H, —C(O)OR$^6$, —CH(OH)R$^6$, or C(O)NR$^6$R$^7$, wherein $R^6$ and $R^7$ are independently hydrogen, optionally substituted alkyl, optionally substituted cycloalkyl, optionally substituted aralkyl, optionally substituted aryl, or optionally substituted heteroaryl.

Diseases that can be treated using the method of the invention include, but are not limited to, atrial fibrillation, atrial flutter, congestive heart failure, epilepsy, stroke, diabetes, obesity, ischemia, stable angina, unstable angina and myocardial infarction. The method of the invention is also useful in treating hyperlipidemic conditions, and is therefore useful for treating metabolic disorders, including type II diabetes, hypertriglyceridemia, and metabolic syndrome. The method of the invention also useful in protecting tissues being maintained for transplantation.

Preferred embodiments of the invention utilize compounds that include, but are not limited to:

ethyl 1-{6-[((3R)oxolan-3-yl)amino]-9-[3,4-dihydroxy-5-(hydroxymethyl)oxolan-2-yl]purin-2-yl}-1,2,3-triazole-4-carboxylate;

2-{6-[((3R)oxolan-3-yl)amino]-2-[4-(hydroxymethyl)(1,2,3-triazolyl)]purin-9-yl}-5-(hydroxymethyl)oxolane-3,4-diol;

2-(6-[((3R)oxolan-3-yl)amino]-2-{4-[4-(trifluoromethyl)phenyl](1,2,3-triazolyl)}purin-9-yl)-5-(hydroxymethyl)oxolane-3,4-diol;

(4S,3R,5R)-2-[6-(cyclopentylamino)-2-(1,2,3,4-tetraazolyl)purin-9-yl]-5-(hydroxymethyl)oxolane-3,4-diol;

ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate;

(1-{9-[(4S,3R,5R)-3,4-dihydroxy-5-(hydroxymethyl)oxolan-2-yl]-6-(cyclopentylamino)purin-2-yl}(1,2,3-triazol-4-yl))-N-methylcarboxamide;

1-{9-[(4S,3R,5R)-3,4-dihydroxy-5-(hydroxymethyl)oxolan-2-yl]-6-(cyclopentylamino)purin-2-yl}-1,2,3-triazole-4-carboxamide;

(4S,3R,5R)-2-{6-(cyclopentylamino)-2-[4-benzyl(1,2,3-triazolyl)]purin-9-yl}-5-(hydroxymethyl)oxolane-3,4-diol;

[(1-{9-[(4S,3R,5R)-3,4-dihydroxy-5-(hydroxymethyl)oxolan-2-yl]-6-(cyclopentylamino)purin-2-yl}(1,2,3-triazol-4-yl))methyl][(4-fluorophenyl)sulfonyl]amine;

[(1-{9-[(4S,3R,5R)-3,4-dihydroxy-5-(hydroxymethyl)oxolan-2-yl]-6-(cyclopentylamino)purin-2-yl}(1,2,3-triazol-5-yl))methyl][(4-fluorophenyl)sulfonyl]amine;

1-{9-[(4S,3R,5R)-3,4-dihydroxy-5-(hydroxymethyl)oxolan-2-yl]-6-(cyclopentylamino)purin-2-yl}-1,2,3-triazole-4-carboxylic acid;

ethyl 1-{9-[(4S,3R,5R)-3,4-dihydroxy-5-(hydroxymethyl)oxolan-2-yl]-6-(cyclohexylamino)purin-2-yl}-1,2,3-triazole-4-carboxylate; and 2-[2-(1H-1,2,3,4-tetraazol-5-yl)-6-(cyclopentylamino)purin-9-yl](2R,5R)-5-(hydroxymethyl)oxolane-3,4-diol.

DEFINITIONS AND GENERAL PARAMETERS

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, for example 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, quaternary amino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or 2) an alkyl group as defined above that is interrupted by 1-5 atoms or groups independently chosen from oxygen, sulfur and —N(R$_a$)$_v$—, where v is 1 or 2 and R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R$^6$ and R$^7$ are independently. R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. Groups such as methyl, ethyl, n-propyl, isopropyl, n-butyl, iso-butyl, t-butyl, n-hexyl, and the like exemplify this term.

The term "substituted lower alkyl" refers to lower alkyl as defined above having 1 to 5 substituents, for example 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, for example having from 1 to 20 carbon atoms, for example 1-10 carbon atoms, more for example 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, for example having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, quaternary amino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or (2) an alkylene group as defined above that is interrupted by 1-5 atoms or groups independently chosen from oxygen, sulfur and —N(R$_a$)$_v$—, where v is 1 or 2 and R$_a$ is chosen from hydrogen, alkyl, cycloalkyl, alkenyl, cycloalkenyl, alkynyl, aryl, heteroaryl, heterocyclyl carbonyl, carboxyester, carboxyamide and sulfonyl.

Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or (3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, isopropoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group for example having from 2 to 20 carbon atoms, more for example 2 to 10 carbon atoms and even more for example 2 to 6 carbon atoms and having 1-6, for example 1, double bond (vinyl). Preferred alkenyl groups include ethenyl or vinyl (—CH=CH$_2$), 1-propylene or allyl (—CH$_2$CH=CH$_2$), isopropylene, (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, quaternary amino, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "alkynyl" refers to a monoradical of an unsaturated hydrocarbon, for example having from 2 to 20 carbon atoms, more for example 2 to 10 carbon atoms and even more for example 2 to 6 carbon atoms and having at least 1 and for example from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, quaternary amino, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, quaternary amino, —SO$_3$H, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, quaternary amino, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1 to 3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "quaternary amino" refers to the group —NRRR where each R is as defined for substituted amino. Any two of the R substituents may be joined to form a heterocyclic group as defined further herein.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, quaternary amino, —SO$_3$H, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or cyclic alkyl groups to which is fused an aryl group, for example indane, and the like.

The term "substituted cycloalkyl" refers to cycloalkyl groups having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, quaternary amino, —SO$_3$H, —SO-alkyl, —SO-aryl, —SO-heteroaryl, —SO$_2$-alkyl, SO2-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, for example 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, substituted amino, quaternary amino, —$SO_3H$, —SO-alkyl, —SO-aryl, —SO-heteroaryl, —$SO_2$-alkyl, $SO_2$-aryl and —$SO_2$-heteroaryl.

Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl).

Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazole, and the like as well as N-alkoxy-nitrogen containing heteroaryl compounds.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, for example 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, quaternary amino, —$SO_3H$, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2. Heterocyclic groups can have a single ring or multiple condensed rings. Preferred heterocyclics include, but are not limited to, tetrahydrofuranyl, morpholino, and piperidinyl.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer, the stereochemistry at each chiral carbon may be specified as either R or S. Resolved compounds whose absolute configuration is unknown are designated (+) or (−) depending on the direction (dextro- or laevorotary) in which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl)amines, tri(substituted alkenyl)amines, cycloalkyl amines, di(cycloalkyl) amines, tri(cycloalkyl)amines, substituted cycloalkyl amines, disubstituted cycloalkyl amine, trisubstituted cycloalkyl amines, cycloalkenyl amines, di(cycloalkenyl) amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279-286), and less likely to cause side effects.

NOMENCLATURE

The naming and numbering of the compounds of the invention is illustrated with a representative compound of Formula I in which $R^1$ is hydroxymethyl 4, $R^2$ is cyclopentyl, $R^3$ is substituted 1,2,3-triazole, and $R^4$ is —C(O)OCH$_2$CH$_3$,:

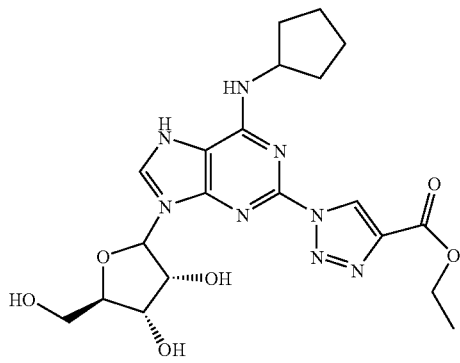

which is named ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate.

THE COMPOUNDS OF THE INVENTION

As presented in the Summary of the Invention, the invention relates to compounds having the structure of Formula I:

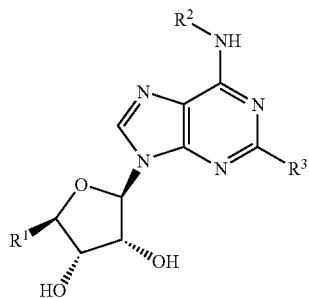

wherein $R^1$, $R^2$, and $R^3$ are as defined above.

As stated previously, $R^1$ is hydroxymethyl, —C(O)OR$^6$, or —C(O)NHR$^6$, in which $R^6$ is hydrogen, optionally substituted alkyl, optionally substituted cycloalkyl, optionally substituted aralkyl, optionally substituted aryl, or optionally substituted heteroaryl. Typically, $R^1$ is hydroxymethyl.

In the Formula I compounds, $R^2$ may be an optionally substituted alkyl, an optionally substituted cycloalkyl, an optionally substituted heterocyclyl, an optionally substituted aryl, or an optionally substituted heteroaryl moiety. In one embodiment, $R^2$ is an optionally substituted heterocyclic moiety. Preferred $R^2$ heterocycles are five membered heterocyclic rings having at least one nitrogen or oxygen atom. Particularly preferred $R^2$ heterocycles include, but are not limited to, optionally substituted pyrrolidine and oxolane rings.

In other embodiments, $R^2$ is an optionally substituted cycloalkyl moiety. Preferably, the cycloalkyl moiety is a five to eight membered ring structure. Examples of suitable cycloalkyl groups include, but are not limited to, cyclopentyl and bicyclo[2.2.1]hept-2-yl structures. In still other embodiments, $R^2$ is an optionally substituted aryl moiety, such as, but not limited to, optionally substituted phenyl and naphthyl rings. When $R^2$ is an optionally substituted alkyl group, it is commonly a $C_{3-20}$ alkyl branched or linear alkyl moiety.

As discussed above, $R^3$ has one of the following structures

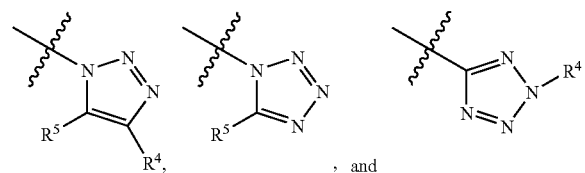

where wherein $R^4$ and $R^5$ are independently chosen from hydrogen, optionally substituted alkyl, optionally substituted aryl, optionally substituted heteroaryl, —CO$_2$H, —SO$_3$H, —C(O)OR$^6$, —CH(OH)R$^6$, or C(O)NR$^6$R$^7$, wherein $R^6$ and $R^7$ are independently hydrogen, optionally substituted alkyl, optionally substituted aralkyl, optionally substituted aryl, or optionally substituted heteroaryl. Preferred $R^4$ and $R^5$ substituents include, but are not limited to, optionally substituted $C_{1-6}$ alkyl groups such as methyl, ethyl, propyl, isopropyl, butyl, benzyl, 4-methylcarboxybenzyl, 4-carboxybenzyl, and hydroxyphenylmethyl; optionally substituted aryl such as methylphenyl; optionally substituted heteroaryl such as pyrazol-4-yl, quinol-2-yl, pyrazin-2-yl, quinazolin-2-yl, pyrid-2-yl, and pyrid-4-yl. Substituted $C_{1-4}$ alkyl groups having terminal quaternary amino of —SO$_3$H groups are also preferred.

When either $R^4$ or $R^5$ is —C(O)OR$^6$, —CH(OH)R$^6$, or —C(O)NR$^6$R$^7$, preferred $R^6$ and $R^7$ substituents include, but are not limited to, hydrogen, optionally substituted $C_{1-4}$ alkyl, including, but not limited to, optionally substituted benzyl groups such as 4-carboxybenzyl, 4-chlorobenzyl, 4-fluorobenzyl, and 3-trifluoromethyl-5-fluorobenzyl, and cycloalkyl groups including, but not limited to, cyclopropyl and cyclcobutyl, Substituted $C_{1-4}$ alkyl groups having terminal quaternary amino of —SO$_3$H groups are also suitable.

Synthetic Reaction Parameters

The terms "solvent", "inert organic solvent" or "inert solvent" means a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

The compounds of the invention are generally synthesized by serial modification of a commercially available protected 2,6-dihalopurine riboside such as acyl-protected 2,6-dichloropurineriboside. The initial step typically involves addition of the $R^2$ moiety by reaction of the protected riboside with an amine of the desired $R^2$ substituent in the presence of base. Once the $R^2$ group has been added, formation of the $R^3$ ring structure begins.

In instances where $R^3$ is a 1,2,3-triazol group, ring formation is accomplished by addition of a hydrazine derivative to the 2 position of the purine residue. The triazole ring is then formed by reaction of the hydrazine-modified purine with an optionally substituted alkyne. If desired, further modification at the $R^5$ and/or $R^4$ position can be accomplished after formation of the ring.

In instances where $R^3$ is a 1,2,3,4-tetrazol group, a commercially available 2-amino purine is used as the starting material. The amino-$R^2$ group is added as discussed above and the resulting compound reacted with sodium azide and acetic acid. If desired, the 5-position on the tetrazol ring may be further modified using conventionally known techniques. For example, the 5-position of the unsubstituted tetrazol ring may be halogenated (Br or I) followed by palladium mediated coupling of the tetrazolylhalide with an aryl-, alkyl-, or vinyl-boronic acid. See *Tetrahedron Letters* (1995) 36(10): 1679-1682.

Alternatively, modification of the 5-position can be accomplished by first reacting the amino purine with an acidic dichloride residue of the desired 5-position moiety followed by conversion to the 5-position substituted tetrazol via a two step process involving treatment with PCl$_5$ (phosphorous pentachloride) followed by sodium azide. See *Asian Journal of Chemistry* (2004), 16(2), 1191-1193.

When R³ is a 2,3,4,5-tetrazol group, a cyano moiety is placed in the 2-position of the purine once the amino-R² group has been added. The tetrazol ring is then formed by reaction of a cyano purine with sodium azide and ammonium chloride. As before, if desired, the tetrazol ring may be further modified using conventionally known techniques. For example, the unsubstituted tetrazol can be alkylated under various conditions with alkyl halides to afford predominantly the N-3 regioisomers. See, *Russian Journal of Organic Chemistry* (2003) 39(5):731-734; *Journal of Medicinal Chemistry* (2004) 47(16):4041-4053; and *European Journal of Medicinal Chemistry* (2004): 39(7):579-592).

It will be appreciated by those of skill in the art that numerous variations of the above-described synthetic route may be derived. For example, modification the R¹ position may be carried out before or after formation of the pyrazole ring.

An example of a method for preparing the compounds of Formula I where R¹ is hydroxymethyl and R³ is a 1,2,3-triazol group is shown in Reaction Scheme I.

REACTION SCHEME I

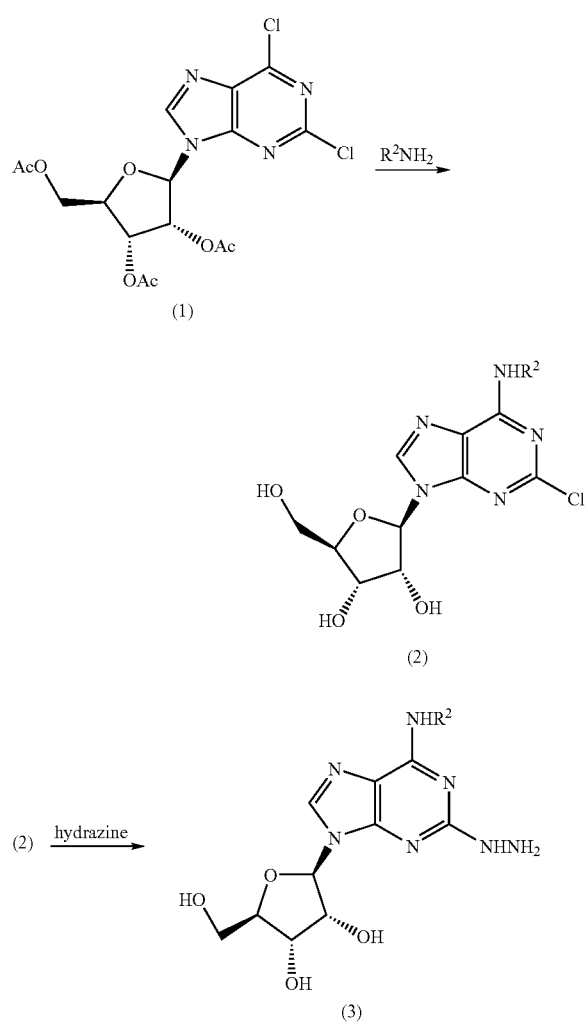

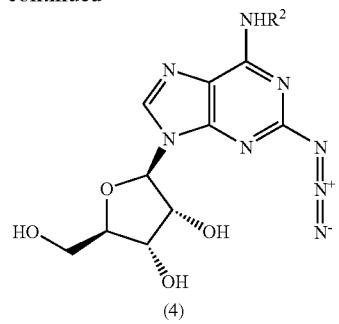

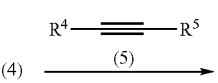

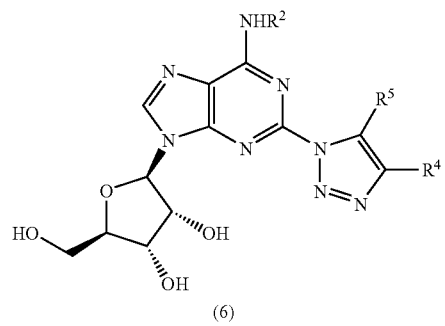

where Ac is acetyl.

Step 1—Preparation of Formula (2)

The compound of formula (2) is prepared by displacement of the 6-chloro of a compound of formula (1), which is prepared as described in J. F. Gorster and R. K. Robins, *J. Org. Chem.* 1966, Vol. 31, 3258-62. The compound of formula (1) is reacted with a compound of formula R²NH₂ in the presence of a base. The reaction is carried out in an inert protic solvent, for example methanol, ethanol, n-butanol, and the like, at a temperature of between room temperature and about reflux, for about 12-48 hours. When the reaction is substantially complete, the product of formula (2) is isolated by conventional means, for example by removal of the solvent under reduced pressure, followed by chromatography of the residue on silica gel. Alternatively, the compound of Formula (2) is used in the next step without purification.

Step 2—Preparation of Formula (3)

The compound of formula (2) is converted to a compound of formula (3) by reaction with hydrazine hydrate. The reaction is carried out with no solvent, or optionally in a protic solvent, for example ethanol, at a temperature of between room temperature and about reflux, for about 12-48 hours. When the reaction is substantially complete, the product of formula (3) is isolated by conventional means, for example by removal of solvent under reduced pressure and trituration the product with ether. Alternatively, the compound of Formula (3) is used in the next step without purification.

Step 3—Preparation of Formula (4)

The compound of formula (3) is converted to a compound of formula (4) by reaction with sodium nitrite. The compound of formula (3) is suspended in water and then an acid, such as acetic acid, is added. The mixture is cooled to approximately 0° C. and sodium nitrite added. The mixture is stirred at 0° C. for approximately 1 to 5 hours and is then allowed to return to room temperature for an additional 8 to 24 hours. When the reaction is substantially complete, the product of formula (4) is isolated by conventional means, for example by extraction with ethyl acetate, removal of solvent under reduced pressure, and triturating the product with ether.

Step 4—Preparation of Formula I

The compound of formula (4) is converted to a compound of Formula I by reaction with an optionally substituted alkyne such as the ethyne derivative of formula (5). The reaction is carried out by suspending N,N-diisopropylethylamine (DIPEA) and the ethyne compound of formula (5) in anhydrous tetrahydrofuran (THF), adding CuI and the compound of formula (4), and then stirring the mixture at room temperature about 24-48 hours. When the reaction is substantially complete, the solvent is evaporated and the residue treated with ethanol and diethyl ether. The resulting solid may be collected by filtration and the product of Formula I is purified by conventional means, for example chromatography. See, Hartmuth et al. (2001); *Angew. Chem. Int. Ed.*, 40:2004-2021.

An example of a method for preparing the compounds of Formula I where $R^1$ is hydroxymethyl and $R^3$ is a 1,2,3,4-tetraazolyl group is shown in Reaction Scheme II.

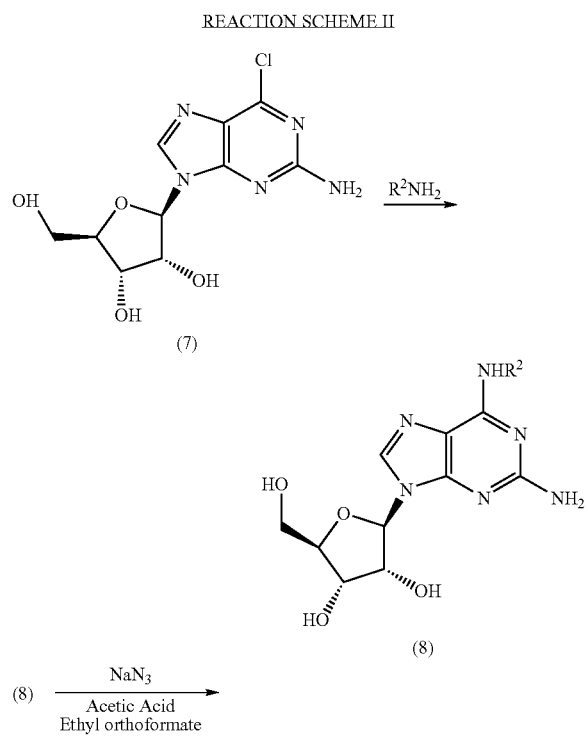

where Ac is acetyl.

Step 1—Preparation of Formula (8)

The compound of formula (8) is prepared by displacement of the 6-chloro of a compound of formula (7), which is prepared using conventional methods such as those described in J. F. Gorster and R. K. Robins, *J. Org. Chem.* 1966, Vol. 31, 3258-62. The compound of formula (7) is reacted with a compound of formula $R^2NH_2$ in the presence of a base. The reaction is carried out in an inert protic solvent, for example methanol, ethanol, n-butanol, and the like, at a temperature of between room temperature and about reflux, for about 12-48 hours. When the reaction is substantially complete, the product of formula (8) is isolated by conventional means, for example by removal of the solvent under reduced pressure, followed by chromatography of the residue on silica gel. Alternatively, the compound of Formula (8) is used in the next step without purification.

Step 2—Preparation of Formula (9)

The compound of formula (8) is converted to a compound of formula (9) by reaction with sodium azide. A mixture of the compound of formula (8), sodium azide, and acetic acid is heated on a steam bath for 1 to 24 hours and then evaporated to dryness. The residue is triturated with water and crystallized to provide the compound of formula (9). The resulting solid may be collected by filtration and the product of Formula I is purified by conventional means, for example chromatography.

An example of a method for preparing the compounds of Formula I where $R^1$ is hydroxymethyl and $R^3$ is a 2,3,4,5-tetrazolyl group is shown in Reaction Scheme III.

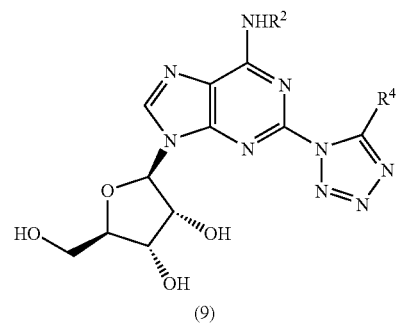

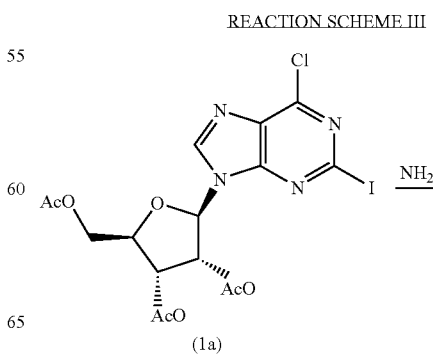

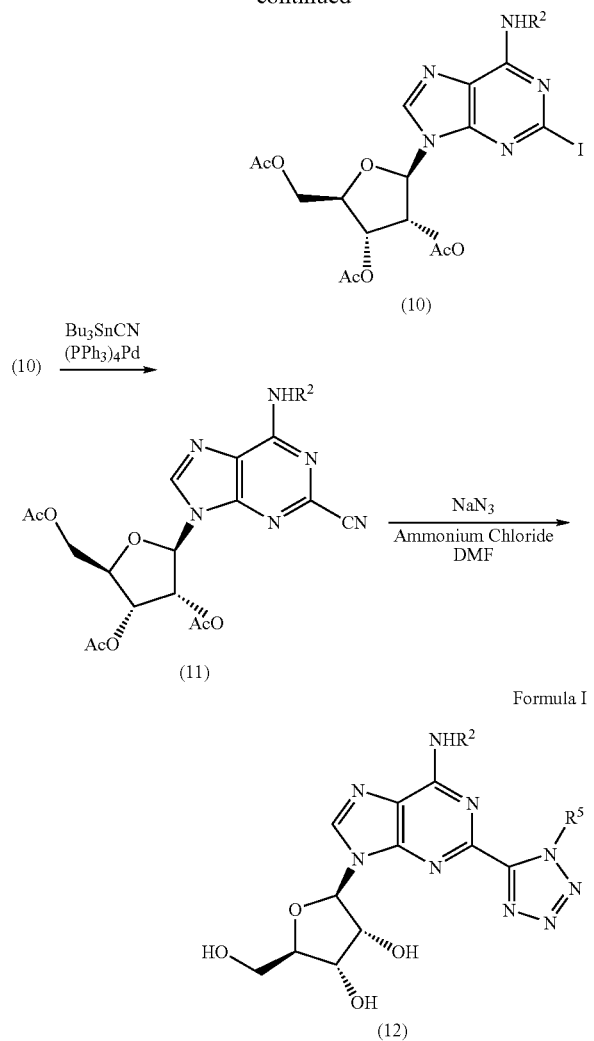

where Ac is acetyl.

Step 1—Preparation of Formula (10)

The compound of formula (10) is prepared by reaction of a 2-iodo-6-chloro compound of formula (1a) with a compound of formula $R^2NH_2$. The reaction is carried out at room temperature for about 12-48 hours. When the reaction is substantially complete, the product of formula (10) is isolated by conventional means, for example by removal of the solvent under reduced pressure, followed by chromatography of the residue on silica gel. Alternatively, the compound of formula (10) is used in the next step without purification.

Step 2—Preparation of Formula (11)

The compound of formula (11) is prepared by displacement of the 2-iodo of a compound of formula (10). The compound of formula (10) is first dissolved in DMF and then reacted with tributyl tin cyanide in the presence of a catalytic amount of tetrakis(triphenylphosphine) palladium. The reaction is carried out at a temperature ranging from approximately 80° C. to approximately 140° C., for about 12-48 hours. When the reaction is substantially complete, the product of formula (I 1) is isolated by conventional means, for example by removal of the solvent under reduced pressure, repeated washing and filtration with ethyl acetate, followed by chromatography of the residue on silica gel.

Step 3—Preparation of Formula (12)

The compound of formula (11) is converted to a compound of formula (12) by reaction with sodium azide. The compound of formula (11) is dissolved in DMF and chilled on an ice bath. To this solution is added sodium azide and ammonium chloride. The resulting mixture is stirred for approximately 0.5 to 2 hours at room temperature and then stirred at 90° C. for an additional 12 to 24 hours. Once the reaction is complete, water is added and the pH of the solution adjusted to approximately 2 by addition of 2M $H_2SO_4$. The product is then extracted using ethyl acetate and the combined organic layers are dried over $NaSO_4$ and the solvent removed by evaporation in vacuum. The resulting solid may be collected by filtration and the product of formula (12) is purified by conventional means, for example chromatography.

Modification of the $R^4$ or $R^5$ Substituent

While desired $R^4$ and $R^5$ substituents can be added via reaction of the appropriately substituted alkyne during formation of the triazole ring, additional modification at these positions can be conducted after the triazole or tetrazol ring has been formed. For example, using a compound of formula (5) in which $R^5$ is hydrogen and $R^4$ is $—CO_2Et$ provides a compound of Formula I in which $R^4$ is 4-ethoxycarbonyl. This ester group can then be hydrolyzed under basic conditions to give the free acid, which in turn can be converted to acid derivatives such as optionally substituted amide by means well known to those skilled in the art, or by the method shown in Reaction Scheme IV.

REACTION SCHEME IV

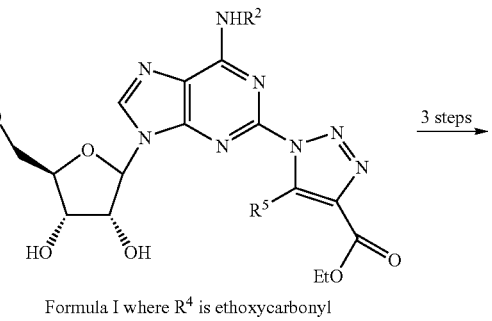

Formula I where $R^4$ is ethoxycarbonyl

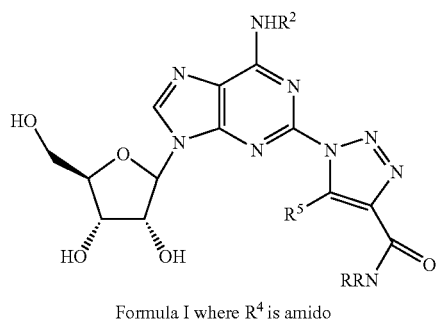

Formula I where $R^4$ is amido

Step 1—Protection of the Compound of Formula I where $R^4$ is Ethoxycarbonyl

The compound of Formula I in which $R^4$ is ethoxycarbonyl is dissolved in a polar solvent, preferably DMF, and imidazole and tertiary butyldimethylsilyl chloride added. The reaction is carried out at a temperature of 50-100° C., for about 12-48 hours. When the reaction is substantially complete, the product is isolated by conventional means, for example by removal of the solvent under reduced pressure, followed by flash chromatography of the residue on silica gel.

Step 2—Hydrolysis of the Ethyl Ester to the Carboxylic Acid

The product from Step 1 is suspended in a mixture of water, an alcohol, and a strong base, preferably potassium hydroxide in methanol. The reaction is carried out at a temperature of 0-40° C., preferably about 25° C., for about 2-5 days, preferably about 3 days. When the reaction is substantially complete, the solvent is removed under reduced pressure, the residue acidified to a pH of about 5, and the product is isolated by conventional means, for example by filtration.

Step 3—Preparation of an Amide

The product from Step 2 is dissolved in an inert solvent, preferably dichloromethane, to which is added HBTU, HOBt, N-methylmorpholine, a catalytic amount of DMAP, and an optionally substituted amine of formula HNRR, as defined above. The reaction is carried out at a temperature of 0-40° C., preferably about 25° C., for about 8-48 hours, preferably about 24 hours. When the reaction is substantially complete, the product is isolated by conventional means.

Step 4—Deprotection

The product from Step 3 is treated with a solution of ammonium fluoride in methanol. The reaction is carried out at a temperature of about reflux, for about 8-48 hours, preferably about 24 hours. When the reaction is substantially complete, the solvent is removed under reduced pressure, the residue acidified to a pH of about 5, and the product is isolated by conventional means, for example by preparative TLC.

Synthesis wherein $R^1$ is —C(O)OR$^6$, or —C(O)NHR$^6$

It will be appreciated by those of skill in the art that modification of the $R^1$ substituent may be conducted after formation of the triazole or tetrazole ring. For example, using a compound of Formula I in which $R^1$ is hydroxymethyl, $R^3$ is 1,2,3-triazol, $R^5$ is hydrogen, and $R^4$ is 4-methylphenyl, one can selectively protect the 3 and 4 position hydroxy groups by reaction with 2,2-dimethoxypropane. The resulting 5' hydroxy compound can then be converted to a optionally substituted carbonyl group via reaction with catalytic amounts of 2,2,6,6-tetramethyl-1-piperidinyloxyl (TEMPO) in combination with [bis(acetoxy)iodo]benzene (BAIB). This carboxylic acid can then be replaced with an optionally substituted carboxamide group and the protecting groups removed using conventional techniques.

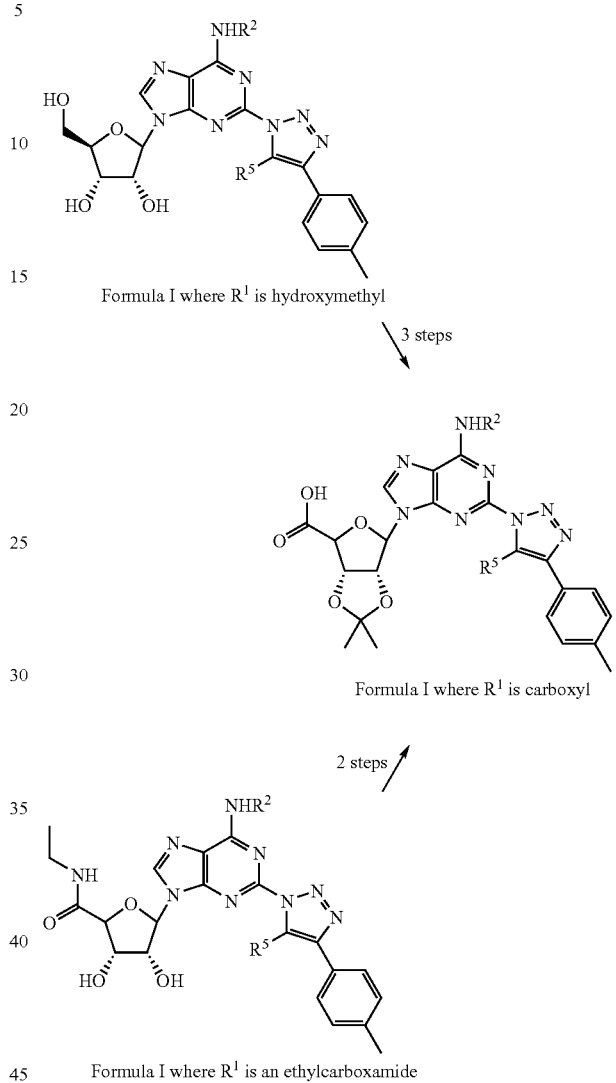

REACTION SCHEME V

Formula I where $R^1$ is hydroxymethyl 3 steps

Formula I where $R^1$ is carboxyl 2 steps

Formula I where $R^1$ is an ethylcarboxamide

UTILITY, TESTING AND ADMINISTRATION

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, and atrial flutter, congestive heart failure, non-insulin-dependent diabetes mellitus, hyperglycemia, epilepsy (anticonvulsant activity), and neuroprotection. $A_1$ adenosine receptor agonists also have antilipolytic effects in adipocytes, which leads to a decreased release of nonesterified fatty acids Testing Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are for example formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. For example, for oral administration, each dosage unit contains from 10 mg to 2 g of a compound of Formula I, more for example from 10 to 700 mg, and for parenteral administration, for example from 10 to 700 mg of a compound of Formula I, more for example about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. For example the compositions are administered by the oral or nasal respiratory route for local or systemic effect. Compositions in for example pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, for example orally or nasally, from devices that deliver the formulation in an appropriate manner.

The following examples are included to demonstrate preferred embodiments of the invention. It should be appreciated by those of skill in the art that the techniques +disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) where $R^1$ is Hydroxymethyl and $R^2$ is Cyclopentyl

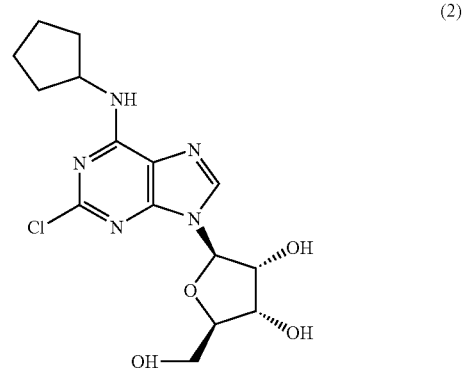

(2)

[3,4-diacetoxy-5-(2,6-dichloropurin-9-yl)oxolan-2-yl] methyl acetate, the compound of formula (1) (2.2 mmol), was suspended in a mixture of 20 mL of ethanol. Triethylamine (20 mmol) and cyclopentyl amine (11.2 mmol) were then added. The solution was brought to reflux for 24 hours.

The solvent was removed under reduced pressure and the residue was dissolved in 100 mL of ethyl acetate and washed twice with 50 mL of water and twice with 10% citric acid. The organic layer was dried over $MgSO_4$ and filtered. The solvent was removed, to afford (4S,2R,3R,5R) 5-[2-chloro-6-(cyclopentylamino)purin-9-yl]-2-(hydroxymethyl)oxolane-3,4-diol, a compound of formula (2).

B. Preparation of a Compound of Formula (2), Varying $R^2$

Similarly, following the procedure of 1A above, but replacing cyclopentyl amine with tetrahydrofuran-3-amine and cyclohexylamine, the following compounds of formula (2) were prepared:

(4S,2R,3R,5R)-5-[2-chloro-6-(oxolan-3-ylamino)purin-9-yl]-2-(hydroxymethyl)oxolane-3,4-diol; and
(4S,2R,3R,5R)-5-[2-chloro-6-(cyclohexylamino)purin-9-yl]-2-(hydroxymethyl)oxolane-3,4-diol.

C. Preparation of a Compound of Formula (2), Varying $R^2$

Similarly, following the procedure of 1A above, but replacing cyclopentyl amine by other compounds of formula $R^2NH_2$, the following compounds of formula (2) are prepared:

(4S,2R,3R,5R)-5-[6-(bicyclo[2.2.1]hept-2-ylamino)-2-chloropurin-9-yl]-2-(hydroxymethyl)oxolane-3,4-diol;
(4S,2R,3R,5R)-5-[6-(benzylamino)-2-chloropurin-9-yl]-2-(hydroxymethyl)oxolane-3,4-diol;
(4S,2R,3R,5R)-5-[6-(cyclopropylmethylamino)-2-chloropurin-9-yl]-2-(hydroxymethyl)oxolane-3,4-diol;
(4S,2R,3R,5R)-5-[6-(cyclopropylamino)-2-chloropurin-9-yl]-2-(hydroxymethyl)oxolane-3,4-diol;
(4S,2R,3R,5R)-5-[6-anilino-2-chloropurin-9-yl]-2-(hydroxymethyl)oxolane-3,4-diol;
(4S,2R,3R,5R)-5-[6-(4-chlorobenzylamino)-2-chloropurin-9-yl]-2-(hydroxymethyl)oxolane-3,4-diol;

(4S,2R,3R,5R)-5-[6-(2-fluorobenzylamino)-2-chloropurin-9-yl]-2-(hydroxymethyl)oxolane-3,4-diol;
(4S,2R,3R,5R)-5-[6-(pyrid-2-ylamino)-2-chloropurin-9-yl]-2-(hydroxymethyl)oxolane-3,4-diol; and
(4S,2R,3R,5R)-5-[6-(pyrrol-3-ylamino)-2-chloropurin-9-yl]-2-(hydroxymethyl)oxolane-3,4-diol.

D. Preparation of a Compound of Formula (2), Varying $R^2$

Similarly, following the procedure of 1A above, but replacing cyclopentylamine by other compounds of formula $R^2NH_2$, other compounds of formula (2) are prepared.

EXAMPLE 2

Preparation of a Compound of Formula (3)

A. Preparation of a Compound of Formula (3) where $R^1$ is Hydroxymethyl and $R^2$ is Cyclopentyl

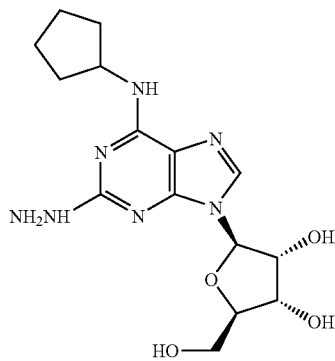

(3)

(4S,2R,3R,5R) 5-[2-chloro-6-(cyclopentylamino)purin-9-yl]-2-(hydroxymethyl)oxolane-3,4-diol, a compound of formula (2) as prepared in Example 1A, was suspended in hydrazine hydrate (5 mL), and the mixture was allowed to stir at room temperature for 24 hours. The hydrazine was removed under reduced pressure and the residue triturated with ether and filtered, to afford (4S,2R,3R,5R)-2-[2-hydrazino-6-(cyclopentylamino)purin-9-yl]-5-(hydroxymethyl)oxolane-3,4-diol, a compound of formula (3), as a white solid.

B. Preparation of a Compound of Formula (3), Varying $R^2$

Similarly, following the procedure of 2A above, but replacing 2-(2-chloro-6-methylaminopurin-9-yl)-5-hydroxymethyltetrahydrofuran-3,4-diol with the tetrahydrofuran-3-amine and cyclohexylamine analogs of formula (2), the following compounds of formula (3) were prepared:
(4S,2R,3R,5R)-5-[2-hydrazino-6-(oxolan-3-ylamino)purin-9-yl]-2-(hydroxymethyl)oxolane-3,4-diol; and
(4S,2R,3R,5R)-5-[6-(cyclohexylamino)-2-hydrazino purin-9-yl]-2-(hydroxymethyl)oxolane-3,4-diol.

C. Preparation of a Compound of Formula (3), Varying $R^2$

Similarly, following the procedure of 2A above, but replacing 2-(2-chloro-6-methylaminopurin-9-yl)-5-hydroxymethyltetrahydrofuran-3,4-diol by other compounds of formula (2), the following compounds of formula (3) are prepared:
(4S,2R,3R,5R)-5-[6-(bicyclo[2.2.1]hept-2-ylamino)-2-hydrazino purin-9-yl]-2-(hydroxymethyl)oxolane-3,4-diol;
(4S,2R,3R,5R)-5-[6-(benzylamino)-2-hydrazinopurin-9-yl]-2-(hydroxymethyl)oxolane-3,4-diol;
(4S,2R,3R,5R)-5-[2-hydrazino-6-(cyclopropylmethylamino)purin-9-yl]-2-(hydroxymethyl)oxolane-3,4-diol;
(4S,2R,3R,5R)-5-[2-hydrazino-6-(cyclopropylamino)purin-9-yl]-2-(hydroxymethyl)oxolane-3,4-diol;
(4S,2R,3R,5R)-5-[2-hydrazino-6-anilinopurin-9-yl]-2-(hydroxymethyl)oxolane-3,4-diol;
(4S,2R,3R,5R)-5-[2-hydrazino-6-(4-chlorobenzylamino)purin-9-yl]-2-(hydroxymethyl)oxolane-3,4-diol;
(4S,2R,3R,5R)-5-[2-hydrazino-6-(2-fluorobenzylamino)purin-9-yl]-2-(hydroxymethyl)oxolane-3,4-diol;
(4S,2R,3R,5R)-5-[2-hydrazino-6-(pyrid-2-ylamino)purin-9-yl]-2-(hydroxymethyl)oxolane-3,4-diol; and
(4S,2R,3R,5R)-5-[2-hydrazino-6-(pyrrol-3-ylamino)purin-9-yl]-2-(hydroxymethyl)oxolane-3,4-diol.

D. Preparation of a Compound of Formula (3), Varying $R^2$

Similarly, following the procedure of 2A above, but replacing 2-(2-chloro-6-cyclopentylaminopurin-9-yl)-5-hydroxymethyltetrahydrofuran-3,4-diol by other compounds of formula (2), other compounds of formula (3) are prepared.

EXAMPLE 3

Preparation of a Compound of Formula (4)

A. Preparation of a Compound of Formula (4) where $R^1$ is Hydroxymethyl and $R^2$ is Cyclopentyl

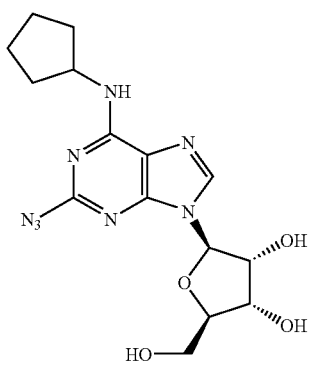

(3)

(4S,2R,3R,5R)-2-[2-hydrazino-6-(cyclopentylamino)purin-9-yl]-5-(hydroxymethyl)oxolane-3,4-diol, a compound of formula (3) as prepared in Example 2A (4.1 mmol), was suspended in 60 ml of water. 3 mL of acetic acid was added and the solution was cooled to 0° C. on an ice-bath. To the cold solution was added sodium nitrite (6 mmol) and the mixture was stirred at 0° C. for 3 hours and then at room temperature for 18 hours. The solution was then extracted twice with 100 mL of ethyl acetic acid. The organic layer was then dried over MgSO$_4$ and the solvent removed. The residue was then triturated in 1:1 ethyl ether:hexane and the solid, (4S,2R,3R,5R)-2-[6-(cyclopentylamino)-2-(azido)purin-9-yl]-5-(hydroxymethyl)oxolane-3,4-diol, collected by filtration.

B. Preparation of a Compound of Formula (4), Varying $R^2$

Similarly, following the procedure of 3A above, but replacing (4S,2R,3R,5R)-2-[2-hydrazino-6-(cyclopentylamino)purin-9-yl]-5-(hydroxymethyl)oxolane-3,4-diol with the tetrahydrofuran-3-amine and cyclohexyl analogs of formula (3), the following compounds of formula (4) were prepared:

(4S,2R,3R,5R)-5-[2-azido-6-(oxolan-3-ylamino)purin-9-yl]-2-(hydroxymethyl)oxolane-3,4-diol; and
(4S,2R,3R,5R)-5-[2-azido-6-(cyclohexylamino)purin-9-yl]-2-(hydroxymethyl)oxolane-3,4-diol.

C. Preparation of a Compound of Formula (4), Varying $R^2$

Similarly, following the procedure of 3A above, but replacing ((4S,2R,3R,5R)-2-[2-hydrazino-6-(cyclopentylamino)purin-9-yl]-5-(hydroxymethyl)oxolane-3,4-diol by other compounds of formula (3), the following compounds of formula (4) are prepared:
(4S,2R,3R,5R)-5-[6-(bicyclo[2.2.1]hept-2-ylamino)-2-azido-purin-9-yl]-2-(hydroxymethyl)oxolane-3,4-diol;
(4S,2R,3R,5R)-5-[6-(benzylamino)-2-azido-purin-9-yl]-2-(hydroxymethyl)oxolane-3,4-diol;
(4S,2R,3R,5R)-5-[2-azido-6-(cyclopropylmethylamino)purin-9-yl]-2-(hydroxymethyl)oxolane-3,4-diol;
(4S,2R,3R,5R)-5-[2-azido-6-(cyclopropylamino)purin-9-yl]-2-(hydroxymethyl)oxolane-3,4-diol;
(4S,2R,3R,5R)-5-[2-azido-6-anilinopurin-9-yl]-2-(hydroxymethyl)oxolane-3,4-diol;
(4S,2R,3R,5R)-5-[2-azido-6-(4-chlorobenzylamino)purin-9-yl]-2-(hydroxymethyl)oxolane-3,4-diol;
(4S,2R,3R,5R)-5-[2-azido-6-(2-fluorobenzylamino)purin-9-yl]-2-(hydroxymethyl)oxolane-3,4-diol;
(4S,2R,3R,5R)-5-[2-azido-6-(pyrid-2-ylamino)purin-9-yl]-2-(hydroxymethyl)oxolane-3,4-diol; and
(4S,2R,3R,5R)-5-[2-azido-6-(pyrrol-3-ylamino)purin-9-yl]-2-(hydroxymethyl)oxolane-3,4-diol.

D. Preparation of a Compound of Formula (3), Varying $R^2$

Similarly, following the procedure of 3A above, but replacing (4S,2R,3R,5R)-2-[2-hydrazino-6-(cyclopentylamino)purin-9-yl]-5-(hydroxymethyl)oxolane-3,4-diol by other compounds of formula (3), other compounds of formula (4) are prepared.

EXAMPLE 4

Preparation of a Compound of Formula I

A. Preparation of a Compound of Formula I where $R^1$ is Hydroxymethyl, $R^2$ is Cyclopentyl, $R^3$ is 1,2,3-Triazole, $R^4$ is Carboxyethyl, and $R^5$ is Hydrogen

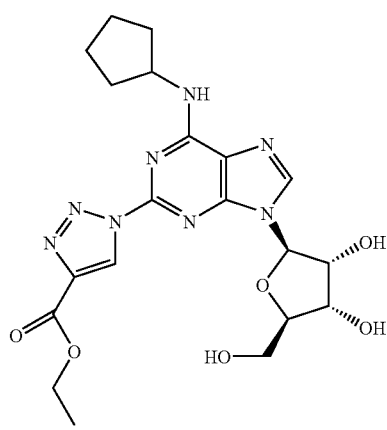

Formula I 0.470 g of diisopropylethylamine and ethyl prop-2-ynoate (1.9 mmol) were dissolved in 20 mL of THF. To the solution was added (4S,2R,3R,5R)-2-[6-(cyclopentylamino)-2-(azido)purin-9-yl]-5-(hydroxymethyl)oxolane-3,4-diol (1.3 mmol) and 350 mg of CuI. The mixture was stirred at room temperature for 24 hours. The solvent was then removed by evaporation and the residue treated with 5 mL of ethanol and ethyl ether. The yellow solid was collected by filtration, and washed with ethanol and ether to afford ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate, a compound of Formula I.

B. Preparation of a Compound of Formula I, Varying $R^2$, $R^3$, and $R^4$

Similarly, following the procedure of 4A above, but optionally replacing (4S,2R,3R,5R)-2-[6-(cyclopentylamino)-2-(azido)purin-9-yl]-5-hydroxymethyl)oxolane-3,4-diol with other compounds of formula (4), and optionally replacing ethyl prop-2-ynoate with other compounds of formula (5), the following compounds of Formula I were prepared:

ethyl 1-{6-[((3R)oxolan-3-yl)amino]-9-[3,4-dihydroxy-5-(hydroxymethyl)oxolan-2-yl]purin-2-yl}-1,2,3-triazole-4-carboxylate;

2-{6-[((3R)oxolan-3-yl)amino]-2-[4-(hydroxymethyl)(1,2,3-triazolyl)]purin-9-yl}-5-(hydroxymethyl)oxolane-3,4-diol;

2-(6-[((3R)oxolan-3-yl)amino]-2-{4-[4-(trifluoromethyl)phenyl](1,2,3-triazolyl)}purin-9-yl)-5-(hydroxymethyl)oxolane-3,4-diol;

(4S,3R,5R)-2-{6-(cyclopentylamino)-2-[4-benzyl(1,2,3-triazolyl)]purin-9-yl}-5-(hydroxymethyl)oxolane-3,4-diol;

[(1-{9-[(4S,3R,5R)-3,4-dihydroxy-5-(hydroxymethyl)oxolan-2-yl]-6-(cyclopentylamino)purin-2-yl}(1,2,3-triazol-4-yl))methyl][(4-fluorophenyl)sulfonyl]amine;

[(1-{9-[(4S,3R,5R)-3,4-dihydroxy-5-(hydroxymethyl)oxolan-2-yl]-6-(cyclopentylamino)purin-2-yl}(1,2,3-triazol-5-yl))methyl][(4-fluorophenyl)sulfonyl]amine; and ethyl 1-{9-[(4S,3R,5R)-3,4-dihydroxy-5-(hydroxymethyl)oxolan-2-yl]-6-(cyclohexylamino)purin-2-yl}-1,2,3-triazole-4-carboxylate.

C. Preparation of a Compound of Formula I, Varying $R^2$, $R^3$, and $R^4$

Similarly, following the procedure of 4A above, but optionally replacing (4S,2R,3R,5R)-2-[6-(cyclopentylamino)-2-(azido)purin-9-yl]-5-(hydroxymethyl)oxolane-3,4-diol with other compounds of formula (4), and optionally replacing ethyl prop-2-ynoate with other compounds of formula (5), the following compounds of Formula I are prepared:

EXAMPLE 5

Preparation of a Compound of Formula I

A. Preparation of a Compound of Formula I where $R^1$ is Hydroxymethyl, $R^2$ is Cyclopentyl, $R^3$ is 1,2,3-Triazole, $R^4$ is Carboxyethyl, and $R^5$ is Hydrogen Formula I

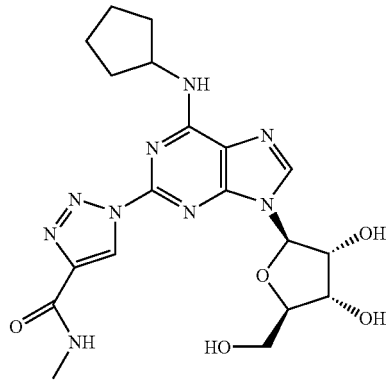

70 mg of the ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate prepared in Example 4A was dissolved in 5 mL of 40% methylamine in water in a sealed tube. The mixture was stirred at 50° C. for 2 hours. A white precipitate formed and was collected by filtration. The collected filtrate was washed with water and ethyl ether to provide the product, (1-{9-[(4S,2R,3R,5R)-3,4-dihydroxy-5-(hydroxymethyl)oxolan-2-yl]-6-(cyclopentylamino)purin-2-yl}(1,2,3-triazol-4-yl))-N-methylcarboxamide ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate.

B. Preparation of a Compound of Formula I, Varying $R^4$

Similarly, following the procedure of 5A above, but optionally replacing ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate with other $R^4$ carboxylate compounds of Formula I, and optionally replacing methylamine with other amines, other compounds of Formula I are prepared.

EXAMPLE 6

Preparation of a Compound of Formula I where $R^1$ is Hydroxymethyl, $R^2$ is Cyclopentyl, $R^3$ is 1,2,3-Triazole $R^4$ is Carboxyethyl, and $R^5$ is Hydrogen Formula I

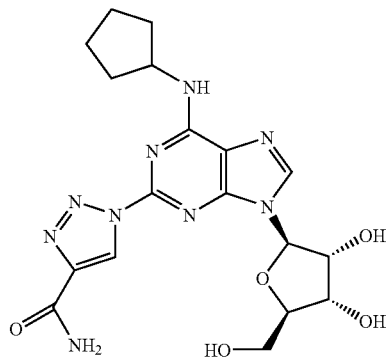

50 mg of the ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate prepared in Example 4A was dissolved in 5 mL of methanol in a tube. Anhydrous $NH_3$ gas was bubbled into the solution for 2 minutes. The tube was then sealed and the mixture was stirred at 50° C. for 24 hours. A white precipitate formed and was collected by filtration. The collected filtrate was washed with water and ethyl ether to provide the product, 1-{9-[(4S,3R,5R)-3,4-dihydroxy-5-(hydroxymethyl)oxolan-2-yl]-6-(cyclopentylamino)purin-2-yl}-1,2,3-triazole-4-carboxamide.

B. Preparation of a Compound of Formula I, Varying $R^4$

Similarly, following the procedure of 6A above, but optionally replacing ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate with other $R^4$ carboxylate compounds of Formula I, other compounds of Formula I are prepared.

EXAMPLE 7

Preparation of a Compound of Formula I

A. Preparation of a Compound of Formula I where $R^1$ is Hydroxymethyl $R^2$ is Cyclopentyl, $R^3$ is 1,2,3-Triazole, $R^4$ is Carboxyl, and $R^5$ is Hydrogen

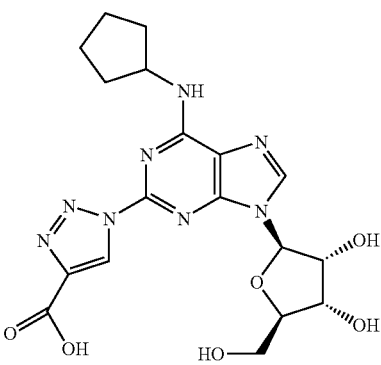

100 mg of the ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate prepared in Example 4A was dissolved in approximately 10 mL of 1 N KOH in methanol. The solution was stirred at 60° C. for 24 hours. The solvent was then removed and the residue dissolved in 5 mL ethyl acetate. The aqueous phase was brought to a pH of 3-4 by addition of 37% HCL. The resulting solid was collected by filtration and washed with water and ether then air dried to provide the product, 1-{9-[(4S,3R,5R)-3,4-dihydroxy-5-(hydroxymethyl)oxolan-2-yl]-6-(cyclopentylamino)purin-2-yl}-1,2,3-triazole-4-carboxylic acid.

B. Preparation of a Compound of Formula I, Varying $R^2$

Similarly, following the procedure of 6A above, but optionally replacing ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate with other $R^4$ carboxylate compounds of Formula I, other compounds of Formula I are prepared.

EXAMPLE 8

Preparation of a Compound of Formula I

A. Preparation of a Compound of Formula I where $R^1$ is Hydroxymethyl, $R^2$ is (3R)Oxolan-3-yl, $R^3$ is 1,2,3-Triazole, $R^4$ is N-Benzylcarboxamide, and $R^5$ is Hydrogen Formula I

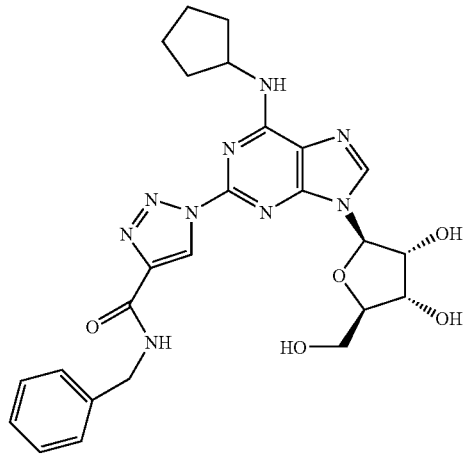

150 mg of 1-{9-[(4S,3R,5R)-3,4-dihydroxy-5-(hydroxymethyl)oxolan-2-yl]-(cyclopentylamino)purin-2-yl}-1,2,3-triazole-4-carboxylic acid prepared according to the method described in Example 7B is dissolved in 5 mL of dimethylformamide(DMF) and mixed with the following:
- 250 mg of 2-(1H-benzotriazo 1-1-yl)-1,1,3,3-tetramethyl uronium hexafluorophosphate (HBTU),
- 100 mg of 1-hydroxybenzotriazole (HOBt),
- 450 mL of benzylamine; and
- a catalytic amount of dimethylaminopyridine (DMAP).

The mixture is stirred overnight at room temperature. The solvent is removed and the residue purified using TLC with a 15:1 dichloromethane:methanol solution to yield (1-{9-[(4S,3R,5R)-3,4-dihydroxy-5-(hydroxymethyl)oxolan-2-yl]-6-(cyclopentylamino)purin-2-yl}-1,2,3-triazole-4-yl)-N-methylcarboxamide.

B. Preparation of a Compound of Formula I, Varying $R^2$

Similarly, following the procedure of 8A above, but optionally replacing 1-{9-[(4S,3R,5R)-3,4-dihydroxy-5-(hydroxymethyl)oxolan-2-yl]-6-(cyclopentylamino)purin-2-yl}-1,2,3-triazole-4-carboxylic acid with other R4 carboxylic acids of Formula I or replacing benzylamine with other desired benzylamine residues, the following compounds of Formula I can be prepared:
methyl 4-{[(1-{6-[((3R)oxolan-3-yl)amino]-9-[(4S,2R,3R,5R)-3,4-dihydroxy-5-(hydroxymethyl)oxolan-2-yl]purin-2-yl}-1,2,3-triazole-4-yl)carbonylamino]methyl}benzoate;

4-{[(1-{6-[((3R)oxolan-3-yl)amino]-9-[(4S,2R,3R,5R)-3,4-dihydroxy-5-(hydroxymethyl)oxolan-2-yl]purin-2-yl}-1,2,3-triazole-4-yl)carbonylamino]methyl}benzoic acid;

(1-{6-[((3R)oxolan-3-yl)amino]-9-[(4S,2R,3R,5R)-3,4-dihydroxy-5-(hydroxymethyl)oxolan-2-yl]purin-2-yl}-1,2,3-triazole-4-yl)-N-[(4-chlorophenyl)methyl]carboxamide;

(1-{6-[((3R)oxolan-3-yl)amino]-9-[(4S,2R,3R,5R)-3,4-dihydroxy-5-(hydroxymethyl)oxolan-2-yl]purin-2-yl}-1,2,3-triazole-4-yl)-N-[(4-fluorophenyl)methyl]carboxamide;

(1-{6-[((3R)oxolan-3-yl)amino]-9-[(4S,2R,3R,5R)-3,4-dihydroxy-5-(hydroxymethyl)oxolan-2-yl]purin-2-yl}-1,2,3-triazole-4-yl)-N-benzylcarboxamide; and (1-{6-[((3R)oxolan-3-yl)amino]-9-[(3 S,2R,4R,5R)-3,4-dihydroxy-5-(hydroxymethyl)oxolan-2-yl]purin-2-yl}-1,2,3-triazole-4-yl)-N-{[5-fluoro-3-(trifluoromethyl)phenyl]methyl}carboxamide.

C. Preparation of a Compound of Formula I, Varying $R^2$

Similarly, following the procedure of 8A above, but optionally replacing 1-{9-[(4S,3R,5R)-3,4-dihydroxy-5-(hydroxymethyl)oxolan-2-yl]-6-(cyclopentylamino)purin-2-yl}-1,2,3-triazole-4-carboxylic acid with other $R^4$ carboxylic acids of Formula I or replacing benzylamine with other desired benzylamine residues, the following compounds of Formula I can be prepared.

EXAMPLE 9

Preparation of a Compound of Formula I vie Secondary Modification of the $R^4$ Substituent A. Protection of the Sugar Residue

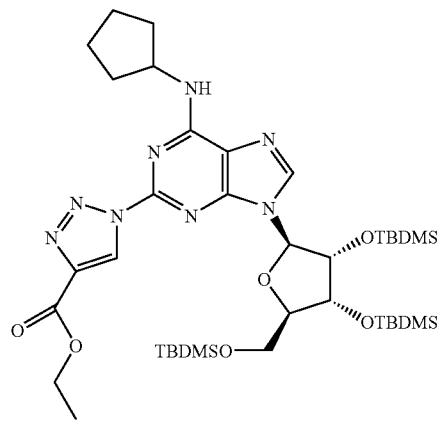

5 g of ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate prepared as described in Example 4A is dissolved in 150 mL of DMF. To this is added 6 g of t-butyldimethylchlorosilane and 3 g of imidazole. The mixture is stirred at 70° C. overnight. The solvent is then evaporated off and the residue purified using TLC with a 20% ethylacetate/hexane solution to yield ethyl 1-(9-{(2R, 3R,4R,5R)-3,4-bis(1,1,1,2,2-tetramethyl-1-silapropoxy)-5-[(1,1,2,2-tetramethyl-1-silapropoxy)methyl]oxolan-2-yl}-6-(cyclopentylamino)purin-2-yl)-1,2,3-triazole-4-carboxylate.

B. Formation of the Alcohol Intermediate

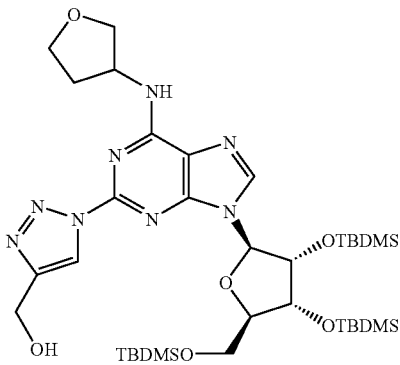

1.5 g of ethyl 1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(cyclopentylamino)purin-2-yl)-1,2,3-triazole-4-carboxylate prepared as described in Example 9A is dissolved in 10 mL of THF and chilled in a 0° C. bath. 2 ml of LiAlH$_4$ is added to this solution. The mixture is then allowed to warm to room temperature over a course of several hours. A saturated solution of NH$_4$Cl is added dropwise to the room temperature solution until no bubbles are observed. The resulting precipitate may be filtered off and the filtrate concentrated down to remove all of the remaining solvent. The remaining aqueous solution is extracted with dichloromethane and the organic layer dried of MgSO$_4$, filtered, and concentrated down to provide the product, [1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(oxolan-3-ylamino)purin-2-yl)-1,2,3-triazole-4-yl]methan-1-ol, was purified by chromatography in a 5% methanol/dichloromethane solution.

C. Formation of the Aldehyde Intermediate

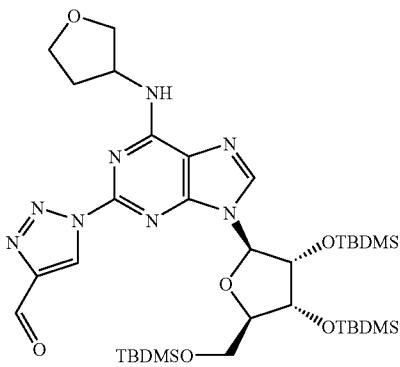

350 mg of pyridinium chlorochromate (PCC) is stirred in 10 mL of dry dichloromethane. In to this suspension, is added 780 mg of the [1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(oxolan-3-ylamino)purin-2-yl)-1,2,3-triazole-4-yl]methan-1-ol prepared in Example 9B. The mixture is stirred at room temperature for 24 hours and filtered. The resulting filtrate is condensed to remove the solvent. The product, 1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(oxolan-3-ylamino)purin-2-yl)-1,2,3-triazole-4-carbaldehyde, is purified by chromatography.

D. Addition of the R$^4$ Substituent

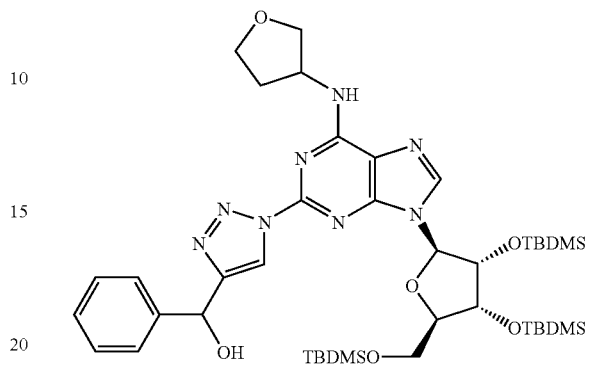

A solution of 500 mg of 1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(oxolan-3-ylamino)purin-2-yl)1,2,3-triazole-4-carbaldehyde, prepared as disclosed in part C above, in 3 mL of THF is chilled in a dry ice/acetone bath. To the chilled solution is added 1.3 mL of a 1 M phenylmagnesium bromide/THF solution in a dropwise fashion. The reaction mixture is then warmed to room temperature over the course of 24 hours. The solvent is then removed and the residue concentrated. The residue is mixed with water and a saturated solution of NH$_4$Cl added. The product, [1-(9-{(2R,3R,4R,5R)-3,4-bis(1,1,2,2-tetramethyl-1-silapropoxy)-5-[(1,1,2,2-tetramethyl-1-silapropoxy)methyl]oxolan-2-yl}-6-(oxolan-3-ylamino)purin-2-yl)-1,2,3-triazole-4-yl]phenylmethan-1-ol, may be extracted with ethyl acetate and purified by chromatography.

E. Deprotection of the Sugar Residue

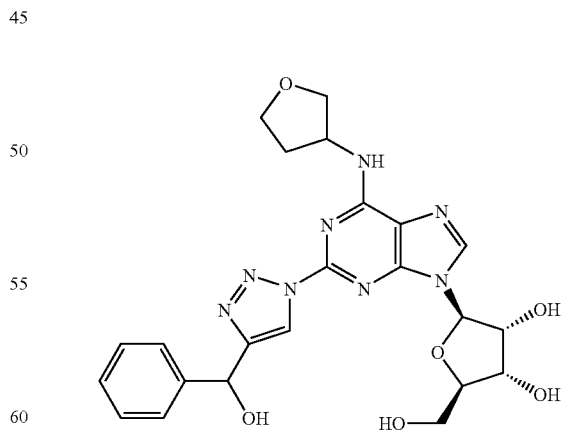

180 mg of the protected product of part D is placed in 3 mL of methanol. To this solution is added 3 mL of 5 M NH$_4$F in methanol. The reaction mixture is held at reflux for 8 hours and the solvent then removed. The residue is purified by chromatography in a 10% methanol/dichloromethane-solution to give the final product, (4S,2R,3R,5R)-5-(hydroxymethyl)-2-{2-[4-(hydroxyphenylmethyl)(1,2,3-triazolyl)]-6-(oxolan-3-ylamino)purin-9-yl}oxolane-3,4-diol.

F. Preparation of a Compound of Formula I, Varying $R^1$, $R^2$, $R^3$, and $R^4$ Similarly, following the procedure of 9A-E above, but optionally replacing ethyl 1-{9-[(4S,3R,5R)-3,4-dihydroxy-5-(hydroxymethyl)oxolan-2-yl]-6-(cyclopentylamino)purin-2-yl}-1,2,3-triazolyl-4-carboxylate with other $R^4$ carboxylates of Formula I or replacing phenylmagnesium bromide with differently-modified magnesium bromide residues, other compounds of Formula I are prepared.

EXAMPLE 10

Preparation of a Compound of Formula I via Modification of the $R^1$ Substituent A. Protection of the 3' and 4' Hydroxyl Moieties on the Sugar Residue

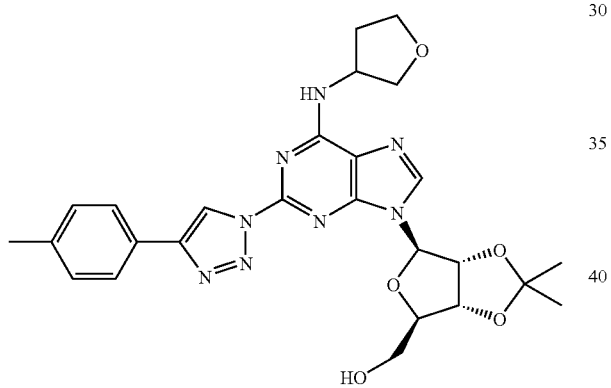

0.500 g of (3S,2R,4R,5R)-2-(hydroxymethyl)-5-{2-[4-(4-methylphenyl)-1,2,3-triazolyl]-6-(oxolan-3-ylamino)purin-9-yl}oxolane-3,4-diol, prepared according to the method described in Example 4, 1.5 mL of 2,2-dimethoxypropane, and 1 mL of a (0.2 g pTSOH/10 mL DMF) solution are mixed in 10 mL of DMF. The solution was heated to 80° C. overnight in a pressure tube.

The following morning, the volatile materials are removed and the acid catalyst quenched by the addition of 10 drops of concentrated $NH_4OH$ solution. The product, ((1R,2R,4R,5R)-7,7-dimethyl-4-{2-[4-(4-methylphenyl)-1,2,3-triazolyl]-6-(oxolan-3-ylamino)purin-9-yl}-3,6,8-trioxabicyclo[3.3.0]oct-2-yl)methan-1-ol, is purified by Biotage™ chromatography (405 cartridge) using stepped 200 mL aliquots of 0%, 5%, 10%, 15%, and 20% methanol in dichloromethane solvent. The product elutes in the 5-15% solvent strength fractions. The material is carried onto the next step without further manipulation.

B. Preparation of the 5' Carboxylic Acid

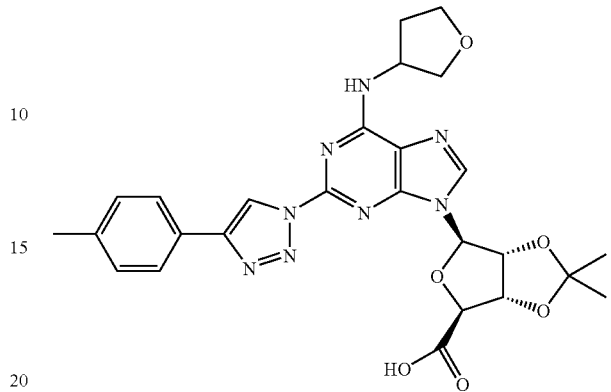

0.5 g of ((1R,2R,4R,5R)-7,7-dimethyl-4-{2-[4-(4-methylphenyl) 1,2,3-triazolyl]-6-(oxolan-3-ylamino)purin-9-yl}-3,6,8-trioxabicyclo[3.3.0]oct-2-yl)methan-1-ol prepared as in Part A above, 30 mg of TEMPO, and 0.7 g of BAIB are combined in a flask, $CH_3CN$ (1.5 mL) and $H_2O$ (1.5 mL) are added and the resulting solution stirred at ambient temperature for 3 hours. The product, (2S,1R,4R,5R)-7,7-dimethyl-4-{2-[4-(4-methylphenyl)-1,2,3-triazolyl]-6-(oxolan-3-ylamino)purin-9-yl}-3,6,8-trioxabicyclo[3.3.0]octane-2-carboxylic acid, precipitates from solution and is collected by filtration and triturated with diethylether.

C. Conversion of the 5' Carboxylic Acid to a 5' Carboxamide

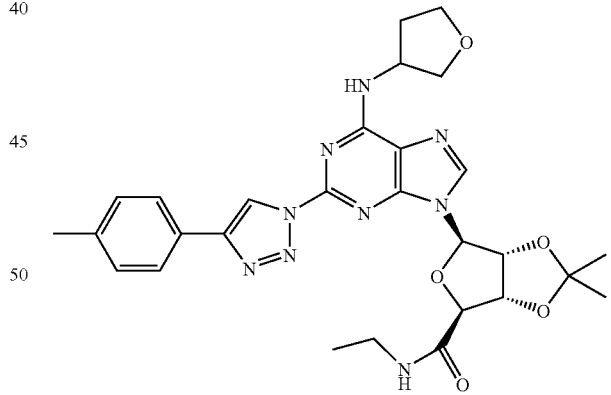

0.1 g of (2S,1R,4R,5R)-7,7-dimethyl-4-{2-[4-(4-methylphenyl) 1,2,3-triazolyl]-6-(oxolan-3-ylamino)purin-9-yl}-3,6,8-trioxabicyclo[3.3.0]octane-2-carboxylic acid, as prepared in Part C above is taken up in 4 mL of dichloromethane. To this solution is added the following:
   0.1 g of 2-(1H-benzotriazo 1-1-yl)-1,1,3,3-tetramethyl uronium hexafluorophosphate (HBTU),
   0.05 g of 1-hydroxybenzotriazole (HOBt),
   a catalytic amount of dimethylaminopyridine (DMAP); and
   0.1 mL of triethylamine.

The mixture was stirred at ambient temperature for 20 minutes and then 0.05 g of ethylamine hydrochloride is added. This mixture is stirred overnight at room temperature.

The following morning the reaction mixture is diluted with 50 mL of dichloromethane and wished with 10 mL of a 10% citric acid solution, 10 mL of $NaHCO_{3(aq)}$, and 10 mL of brine. The organic solution is dried over $MgSO_4$. The solvent is then removed on a rotovap and the product purified by prep TLC using 10% methanol in dichloromethane to yield ((2S, 1R,4R,5R)-7,7-dimethyl-4-{2-[4-(4-methylphenyl) 1,2,3-triazolyl]-6-(oxolan-3-ylamino)purin-9-yl}-3,6,8-trioxabicyclo[3.3.0]oct-2-yl)-N-ethylcarboxyamide.

D. Deprotection of the 3' and 4' Hydroxyl Moieties on the Sugar Residue

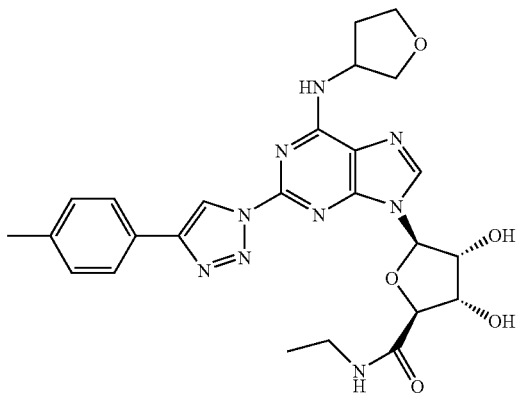

70 mg of a 3',4' protected carboxamide prepared as described in Part C above, ((2S,1R,4R,5R)-7,7-dimethyl-4-{2-[4-(4-methylphenyl) 1,2,3-triazolyl]-6-(oxolan-3-ylamino)purin-9-yl}-3,6,8-trioxabicyclo[3.3.0]oct-2-yl)-N-ethylcarboxamide, is taken up in acetic acid (4 mL) and $H_2O$ (1 mL). The resulting solution is heated at 80° C. overnight. The following morning, the reaction mixture is cooled to room temperature.

The solvents are removed on a rotovap and the resulting solid taken up in methanol. Any solid remaining insoluble is collected via filtration. The mother liquor is used to spot a prep TLC plate that was eluted using 10% methanol in dichloromethane as the eluent. The lower fluorescent spot is collected. After desorption and solvent removal, an additional amount of product may be recovered. This product and the initial insoluble product are confirmed by GC/MS to be ((2S,3S,4R,5R)-3,4-dihydroxy-5-{2-[4-(4-methylphenyl) 1,2,3-triazolyl]-6-(oxolan-3-ylamino)purin-9-yl}oxolan-2-yl)-N-ethylcarboxamide.

E. Preparation of Other Compounds of Formula I, Varying $R^1$, $R^2$, and $R^4$

Similarly, following the procedure of 10A-C or 10A-D above, but optionally replacing (3S,2R,4R,5R)-2-(hydroxymethyl)-5-{2-[4-(4-methylphenyl) 1,2,3-triazolyl]-6-(oxolan-3-ylamino)purin-9-yl}oxolane-3,4-diol with other $R^1$ hydroxymethyl compounds of Formula I and optionally replacing the ethylamine hydrochloride, the following other compounds were prepared:

5-{6-[((3R)oxolan-3-yl)amino]-2-(4-(2-quinolyl)-1,2,3-triazolyl)purin-9-yl}(2S,4S,3R,5R)-3,4-dihydroxyoxolane-2-carboxylic acid;

5-{6-[((3R)oxolan-3-yl)amino]-2-(4-(4-pyridyl)-1,2,3-triazolyl)purin-9-yl}(2S,4S,3R,5R)-3,4-dihydroxyoxolane-2-carboxylic acid (5-{6-[((3R)oxolan-3-yl)amino]-2-(4-(2-quinolyl)-1,2,3-triazolyl)purin-9-yl}(2S,4S,3R,5R)-3,4-dihydroxyoxolan-2-yl)-N-ethylcarboxamide; and (5-{6-[((3R)oxolan-3-yl)amino]-2-(4-(4-pyridyl)-1,2,3-triazolyl)purin-9-yl}(2S,4S,3R,5R)-3,4-dihydroxyoxolan-2-yl)-N-ethylcarboxamide.

D. Preparation of Other Compounds of Formula I, Varying $R^1$, $R^2$ $R^3$, $R^4$, and $R^5$ Similarly, following the procedure of 10A-C or 10A-D above, but optionally replacing (3S,2R,4R,5R)-2-(hydroxymethyl)-5-{2-[4-(4-methylphenyl)-1,2,3-triazolyl]-6-(oxolan-3-ylamino)purin-9-yl}oxolane-3,4-diol with other $R^1$ hydroxymethyl compounds of Formula I and optionally replacing the ethylamine hydrochloride with other amine salts, other compound of Formula I are prepared.

EXAMPLE 12

Preparation of a Compound of Formula (8)

A. Preparation of a Compound of Formula (8) where $R^1$ is Hydroxymethyl and $R^2$ is Cyclopentyl

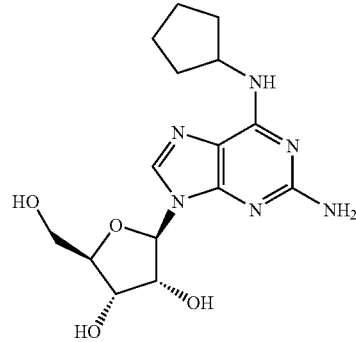

To suspension of (4S,2R,3R,5R)-2-[2-amino-6-chloropurin-9-yl]-5-(hydroxymethyl)oxolane-3,4-diol in 15 mL of ethanol was added 0.4 g of cyclopentyl amine and 10 mmol of trimethyl amine. The mixture was stirred at 80° C. for 24 hours. The residue was purified using preparative thin layer chromatography (15:1 dichloromethane:methanol) to yield (4S,2R,3R,5R)-2-[2-amino-6-(cyclopentylamino)purin-9-yl]-5-(hydroxymethyl)oxolane-3,4-diol, a compound of formula (8).

B. Preparation of a Compound of Formula (8), Varying $R^2$

Similarly, following the procedure of 12A above, but replacing cyclopentyl amine with tetrahydrofuran-3-amine and cyclohexylamine, the following compounds of formula (2) are prepared:

(4S,2R,3R,5R)-5-[2-amino-6-(oxolan-3-ylamino)purin-9-yl]-2-(hydroxymethyl)oxolane-3,4-diol; and (4S,2R,3R,5R)-5-[2-amino-6-(cyclohexylamino)purin-9-yl]-2-(hydroxymethyl)oxolane-3,4-diol.

C. Preparation of a Compound of Formula (2), Varying R²

Similarly, following the procedure of 1A above, but replacing cyclopentyl amine by other compounds of formula R²NH₂, the following compounds of formula (2) are prepared:
(4S,2R,3R,5R)-5-[6-(ethylamino)-2-aminopurin-9-yl]-2-(hydroxymethyl)oxolane-3,4-diol;
(4S,2R,3R,5R)-5-[6-(methylamino)-2-aminopurin-9-yl]-2-(hydroxymethyl)oxolane-3,4-diol;
(4S,2R,3R,5R)-5-[6-(bicyclo[2.2.1]hept-2-ylamino)-2-aminopurin-9-yl]-2-(hydroxymethyl)oxolane-3,4-diol;
(4S,2R,3R,5R)-5-[6-(benzylamino)-2-aminopurin-9-yl]-2-(hydroxymethyl)oxolane-3,4-diol;
(4S,2R,3R,5R)-5-[6-(n-propylamino)-2-aminopurin-9-yl]-2-(hydroxymethyl)oxolane-3,4-diol;
(4S,2R,3R,5R)-5-[6-(cyclopropylmethylamino)-2-aminopurin-9-yl]-2-(hydroxymethyl)oxolane-3,4-diol;
(4S,2R,3R,5R)-5-[6-(cyclopropylamino)-2-aminopurin-9-yl]-2-(hydroxymethyl)oxolane-3,4-diol;
(4S,2R,3R,5R)-5-[6-anilino-2-aminopurin-9-yl]-2-(hydroxymethyl)oxolane-3,4-diol;
(4S,2R,3R,5R)-5-[6-(4-chlorobenzylamino)-2-aminopurin-9-yl]-2-(hydroxymethyl)oxolane-3,4-diol;
(4S,2R,3R,5R)-5-[6-(2-fluorobenzylamino)-2-aminopurin-9-yl]-2-(hydroxymethyl)oxolane-3,4-diol;
(4S,2R,3R,5R)-5-[6-(pyrid-2-ylamino)-2-aminopurin-9-yl]-2-(hydroxymethyl)oxolane-3,4-diol; and
(4S,2R,3R,5R)-5-[6-(pyrrol-3-ylanino)-2-aminopurin-9-yl]-2-(hydroxymethyl)oxolane-3,4-diol.

D. Preparation of a Compound of Formula (8), Varying R²

Similarly, following the procedure of 12A above, but replacing cyclopentylamine by other compounds of formula R²NH₂, other compounds of formula (8) are prepared.

EXAMPLE 13

Preparation of a Compound of Formula I

A. Preparation of a Compound of Formula I where R¹ is Hydroxymethyl R² is Cyclopentyl, and R³ is 1,2,3,4-Tetrazolyl

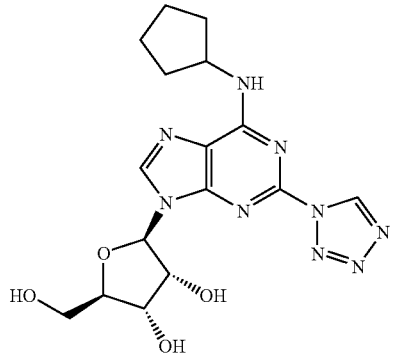

Formula I (4S,2R,3R,5R)-2-[2-amino-6-(cyclopentylamino)purin-9-yl]-5-(hydroxymethyl)oxolane-3,4-diol 100 mg), a compound of formula (8) as prepared in Example 12A, was suspended in trimethyl orthoformate (1 mL) and actate (2 mL). To this solution was added 50 mg of sodium azide. The mixture was stirred at 95° C. for 24 hours. The compound was purified using preparatory thin layer chromatography, to afford (4S,2R,3R,5R)-2-[6-(cyclopentylamino)-2-(1,2,3,4-tetraazolyl)purin-9-yl]-5-(hydroxymethyl)oxolane-3,4-diol, a compound of Formula I.

B. Preparation of a Compound of Formula I, Varying R²

Similarly, following the procedure of 13A above, but replacing (4S,2R,3R,5R)-2-[2-amino-6-(cyclopentylamino)purin-9-yl]-5-(hydroxymethyl)oxolane-3,4-diol with the tetrahydrofuran-3-amine and cyclohexylamine analogs of formula (8), the following compounds of Formula I are prepared:
(4S,2R,3R,5R)-5-[6-(1,2,3,4-tetraazolyl)-(oxolan-3-ylamino)purin-9-yl]-2-(hydroxymethyl)oxolane-3,4-diol; and
(4S,2R,3R,5R)-5-[6-(cyclohexylamino)-2-(1,2,3,4-tetraazolyl)purin-9-yl]-2-(hydroxymethyl)oxolane-3,4-diol.

C. Preparation of a Compound of Formula I, Varying R²

Similarly, following the procedure of 13A above, but replacing (4S,2R,3R,5R)-2-[2-amino-6-(cyclopentylamino)purin-9-yl]-5-(hydroxymethyl)oxolane-3,4-diol by other compounds of formula (8), the following compounds of Formula I are prepared:
(4S,2R,3R,5R)-5-[2-(1,2,3,4-tetraazolyl)-6-(ethylamino)purin-9-yl]-2-(hydroxymethyl)oxolane-3,4-diol;
(4S,2R,3R,5R)-5-[2-(1,2,3,4-tetraazolyl)-6-(methylamino)purin-9-yl]-2-(hydroxymethyl)oxolane-3,4-diol;
(4S,2R,3R,5R)-5-[2-(1,2,3,4-tetraazolyl)-6-(n-propylamino)purin-9-yl]-2-(hydroxymethyl)oxolane-3,4-diol;
(4S,2R,3R,5R)-5-[6-(bicyclo[2.2.1]hept-2-ylamino)-2-(1,2,3,4-tetraazolyl)purin-9-yl]-2-(hydroxymethyl)oxolane-3,4-diol;
(4S,2R,3R,5R)-5-[6-(benzylamino)-2-(1,2,3,4-tetraazolyl)purin-9-yl]-2-(hydroxymethyl)oxolane-3,4-diol;
(4S,2R,3R,5R)-5-[2-(1,2,3,4-tetraazolyl)-6-(cyclopropylmethylamino)purin-9-yl]-2-(hydroxymethyl)oxolane-3,4-diol;
(4S,2R,3R,5R)-5-[2-(1,2,3,4-tetraazolyl)-6-(cyclopropylamino)purin-9-yl]-2-(hydroxymethyl)oxolane-3,4-diol;
(4S,2R,3R,5R)-5-[2-(1,2,3,4-tetraazolyl)-6-anilinopurin-9-yl]-2-(hydroxymethyl)oxolane-3,4-diol;
(4S,2R,3R,5R)-5-[2-(1,2,3,4-tetraazolyl)-6-(4-chlorobenzylamino)purin-9-yl]-2-(hydroxymethyl)oxolane-3,4-diol;
(4S,2R,3R,5R)-5-[2-(1,2,3,4-tetraazolyl)-6-(2-fluorobenzylamino)purin-9-yl]-2-(hydroxymethyl)oxolane-3,4-diol;
(4S,2R,3R,5R)-5-[2-(1,2,3,4-tetraazolyl)-6-(pyrid-2-ylamino)purin-9-yl]-2-(hydroxymethyl)oxolane-3,4-diol; and
(4S,2R,3R,5R)-5-[2-(1,2,3,4-tetraazolyl)-6-(pyrrol-3-ylamino)purin-9-yl]-2-(hydroxymethyl)oxolane-3,4-diol.

D. Preparation of a Compound of Formula I, Varying R²

Similarly, following the procedure of 13A above, but replacing (4S,2R,3R,5R)-2-[2-amino-6-(cyclopentylamino)purin-9-yl]-5-(hydroxymethyl)oxolane-3,4-diol by other compounds of formula (8), other compounds of Formula I are prepared.

EXAMPLE 14

Preparation of a Compound of Formula (10)

A. Preparation of a Compound of Formula (10) where $R^2$ is Cyclopentyl

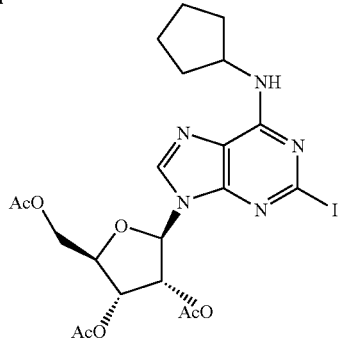

1.15 g of [(2R,3R,4R,5R)-3,4-diacetyloxy-5-(6-chloro-2-iodopurin-9-yl)oxolan-2-yl]methyl acetate (Toronto Research Chemicals) was placed in 20 mL of DMF (dimethylformamide) and stirred. To this solution was added 0.42 mL of cyclopentyl amine and 10 mL of DIPEA (diisopropylethylamine). The resulting mixture was stirred overnight at room temperature. The next morning, the solvent was removed and the residue purified using a dichloromethane/methanol 20:1 column to provide (2R,3R,4R,5R)-4-acetyloxy-2-(acetyloxymethyl)-5-[6-(cyclopentylamino)-2-iodopurin-9-yl]oxolan-3-yl acetate, a compound of formula (10).

B. Preparation of a Compound of Formula (10), Varying $R^2$

Similarly, following the procedure of 14A above, but replacing cyclopentyl amine with tetrahydrofuran-3-amine and cyclohexylamine, the following compounds of formula (10) are prepared:
(2R,3R,4R,5R)-4-acetyloxy-2-(acetyloxyrnethyl)-5-[6-(oxolan-3-ylamino)-2-iodopurin-9-yl]oxolan-3-yl acetate; and
(2R,3R,4R,5R)-4-acetyloxy-2-(acetyloxymethyl)-5-[6-(cyclohexylamino)-2-iodopurin-9-yl]oxolan-3-yl acetate.

C. Preparation of a Compound of Formula (10), Varying $R^2$

Similarly, following the procedure of 14A above, but replacing cyclopentyl amine by other compounds of formula $R^2NH_2$, the following compounds of formula (10) are prepared:
(2R,3R,4R,5R)-4-acetyloxy-2-(acetyloxymethyl)-5-[6-(ethylamino)-2-iodopurin-9-yl]oxolan-3-yl acetate
(2R,3R,4R,5R)-4-acetyloxy-2-(acetyloxymethyl)-5-[6-(methylamino)-2-iodopurin-9-yl]oxolan-3-yl acetate;
(2R,3R,4R,5R)-4-acetyloxy-2-(acetyloxymethyl)-5-[6-(bicyclo[2.2.1]hept-2-ylamino)-2-iodopurin-9-yl]oxolan-3-yl acetate;
(2R,3R,4R,5R)-4-acetyloxy-2-(acetyloxymethyl)-5-[6-(benzylamino)-2-iodopurin-9-yl]oxolan-3-yl acetate;
(2R,3R,4R,5R)-4-acetyloxy-2-(acetyloxymethyl)-5-[6-(n-propylamino)-2-iodopurin-9-yl]oxolan-3-yl acetate;
(2R,3R,4R,5R)-4-acetyloxy-2-(acetyloxymethyl)-5-[6-(cyclopropylmethylamino)-2-iodopurin-9-yl]oxolan-3-yl acetate;
(2R,3R,4R,5R)-4-acetyloxy-2-(acetyloxymethyl)-5-[6-(cyclopropylamino)-2-iodopurin-9-yl]oxolan-3-yl acetate;
(2R,3R,4R,5R)-4-acetyloxy-2-(acetyloxymethyl)-5-[6-anilino-2-iodopurin-9-yl]oxolan-3-yl acetate;
(2R,3R,4R,5R)-4-acetyloxy-2-(acetyloxymethyl)-5-[6-(4-chlorobenzylamino)-2-iodopurin-9-yl]oxolan-3-yl acetate;
(2R,3R,4R,5R)-4-acetyloxy-2-(acetyloxymethyl)-5-[6-(2-fluorobenzylamino)-2-iodopurin-9-yl]oxolan-3-yl acetate;
(2R,3R,4R,5R)-4-acetyloxy-2-(acetyloxymethyl)-5-[6-(pyrid-2-ylamino)-2-iodopurin-9-yl]oxolan-3-yl acetate; and
(2R,3R,4R,5R)-4-acetyloxy-2-(acetyloxymethyl)-5-[6-(pyrrol-3-ylamino)-2-iodopurin-9-yl]oxolan-3-yl acetate.

D. Preparation of a Compound of Formula (10), Varying $R^2$

Similarly, following the procedure of 14A above, but replacing cyclopentylamine by other compounds of formula $R^2NH_2$, other compounds of formula (10) are prepared.

EXAMPLE 15

Preparation of a Compound of Formula (11)

A. Preparation of a Compound of Formula (11) where $R^2$ is Cyclopentyl

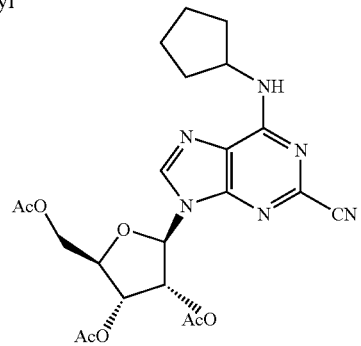

(2R,3R,4R,5R)-4-acetyloxy-2-(acetyloxymethyl)-5-[6-(cyclopentylamino)-2-iodopurin-9-yl]oxolan-3-yl acetate (1.53 mmol), a compound of formula (10) as prepared in Example 14A, was suspended in DMF (40 mL). To this solution was added 50 mg of 0.058 g of tributyl tin cyanide and 0.27 g of tetrakis (triphenylphosphine) palladium. The resulting mixture was stirred at 120° C. overnight.

The compound was concentrated via evaporation and the residue then dissolved in ethyl acetate, filtered, rewashed with ethyl acetate, and filtered once more. The filtrate was then concentrated and purified using preparatory thin layer chromatography, to afford (2R,3R,4R,5R)-4-acetyloxy-2-(acetyloxymethyl)-5-[6-(cyclopentylamino)-2-cyanopurin-9-yl]oxolan-3-yl acetate, a compound of Formula (11).

B. Preparation of a Compound of Formula (11), Varying $R^2$

Following the procedure of 15A above, but replacing (2R,3R,4R,5R)-4-acetyloxy-2-(acetyloxymethyl)-5-[6-(cyclopentylamino)-2-iodopurin-9-yl]oxolan-3-yl acetate with the tetrahydrofuran-3-amine and cyclohexylamine analogs of formula (10), the following compounds of formula (11) are prepared:
(2R,3R,4R,5R)-4-acetyloxy-2-(acetyloxymethyl)-5-[6-(oxolan-3-ylamino)-2-cyanopurin-9-yl]oxolan-3-yl acetate; and
(2R,3R,4R,5R)-4-acetyloxy-2-(acetyloxymethyl)-5-[6-(cyclohexylamino)-2-cyanopurin-9-yl]oxolan-3-yl acetate.

C. Preparation of a Compound of Formula (11), Varying $R^2$

Following the procedure of 15A above, but replacing (2R,3R,4R,5R)-4-acetyloxy-2-(acetyloxymethyl)-5-[6-(cyclopentylamino)-2-iodopurin-9-yl]oxolan-3-yl acetate by other compounds of formula (10), the following compounds of formula (11) are prepared:

(2R,3R,4R,5R)-4-acetyloxy-2-(acetyloxymethyl)-5-[6-(ethylamino)-2-cyanopurin-9-yl]oxolan-3-yl acetate (2R,3R,4R,5R)-4-acetyloxy-2-(acetyloxymethyl)-5-[6-(methylamino)-2-cyanopurin-9-yl]oxolan-3-yl acetate;

(2R,3R,4R,5R)-4-acetyloxy-2-(acetyloxymethyl)-5-[6-(bicyclo[2.2.1]hept-2-ylamino)-2-cyanopurin-9-yl]oxolan-3-yl acetate;

(2R,3R,4R,5R)-4-acetyloxy-2-(acetyloxymethyl)-5-[6-(benzylamino)-2-cyanopurin-9-yl]oxolan-3-yl acetate;

(2R,3R,4R,5R)-4-acetyloxy-2-(acetyloxymethyl)-5-[6-(n-propylamino)-2-cyanopurin-9-yl]oxolan-3-yl acetate;

(2R,3R,4R,5R)-4-acetyloxy-2-(acetyloxymethyl)-5-[6-(cyclopropylmethylamino)-2-cyanopurin-9-yl]oxolan-3-yl acetate;

(2R,3R,4R,5R)-4-acetyloxy-2-(acetyloxymethyl)-5-[6-(cyclopropylamino)-2-cyanopurin-9-yl]oxolan-3-yl acetate;

(2R,3R,4R,5R)-4-acetyloxy-2-(acetyloxymethyl)-5-[6-anilino-2-cyanopurin-9-yl]oxolan-3-yl acetate;

(2R,3R,4R,5R)-4-acetyloxy-2-(acetyloxymethyl)-5-[6-(4-chlorobenzylamino)-2-cyanopurin-9-yl]oxolan-3-yl acetate;

(2R,3R,4R,5R)-4-acetyloxy-2-(acetyloxymethyl)-5-[6-(2-fluorobenzylamino)-2-cyanopurin-9-yl]oxolan-3-yl acetate;

(2R,3R,4R,5R)-4-acetyloxy-2-(acetyloxymethyl)-5-[6-(pyrid-2-ylamino)-2-cyanopurin-9-yl]oxolan-3-yl acetate; and (2R,3R,4R,5R)-4-acetyloxy-2-(acetyloxymethyl)-5-[6-(pyrrol-3-ylamino)-2-cyanopurin-9-yl]oxolan-3-yl acetate.

D. Preparation of a Compound of Formula I, Varying $R^2$

Similarly, following the procedure of 15A above, but replacing (2R,3R,4R,5R)-4-acetyloxy-2-(acetyloxymethyl)-5-[6-(cyclopentylamino)-2-iodopurin-9-yl]oxolan-3-yl acetate by other compounds of formula (10), other compounds of formula (11) are prepared.

EXAMPLE 16

Preparation of a Compound of Formula I

A. Preparation of a Compound of Formula I where $R^1$ is Hydroxymethyl $R^2$ is Cyclopentyl, and $R^3$ is 2,3,4,5-Tetrazolyl Formula I

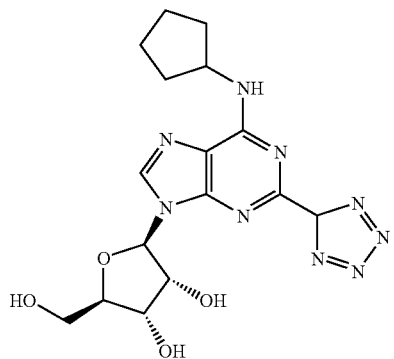

A suspension of (2R,3R,4R,5R)-4-acetyloxy-2-(acetyloxymethyl)-5-[6-(cyclopentylamino)-2-cyanopurin-9-yl]oxolan-3-yl acetate, (0.5 mmol), a compound of formula (11) as prepared in Example 15A, in DMF (20 mL) was cooled to 0° C. in an ice bath. To this was added 0.125 mmol of ammonium chloride followed 1 mmol of sodium azide. The resulting mixture was allowed to warm to room temperature and then stirred at room temperature for 0.5 hours. After which, the mixture was stirred at 90° C. overnight.

The following morning, the reaction was brought to 0° C. using an ice bath. Once chilled, 10 mL of a 10% aqueous solution of sodium nitrite was added to the chilled mixture, which was then stirred for 1 hour. At this point, 20 mL of water was added and the pH of the solution adjusted to 2 using 2M $H_2SO_4$. The product was then extracted using ethyl acetate and the combined organic layers were dried over $NaSO_4$. The solvent was removed by evaporation in vacuum. The compound was purified using preparatory thin layer chromatography, to afford (4S,2R,3R,5R)-2-[6-(cyclopentylamino)-2-(1,2,3,4-tetraazolyl)purin-9-yl]-5-(hydroxymethyl)oxolane-3,4-diol, a compound of Formula I.

B. Preparation of a Compound of Formula I, Varying $R^2$

Similarly, following the procedure of 16A above, but replacing (2R,3R,4R,5R)-4-acetyloxy-2-(acetyloxymethyl)-5-[6-(cyclopentylamino)-2-cyanopurin-9-yl]oxolan-3-yl acetate with the tetrahydrofuran-3-amine and cyclohexylamine analogs of formula (11), the following compounds of Formula I were prepared:

(4S,2R,3R,5R)-2-[6-(oxolan-3-ylamino)-2-(1,2,3,4-tetraazolyl)purin-9-yl]-5-(hydroxymethyl)oxolane-3,4-diol; and (4S,2R,3R,5R)-2-[6-(cyclohexylamino)-2-(1,2,3,4-tetraazolyl)purin-9-yl]-5-(hydroxymethyl)oxolane-3,4-diol.

C. Preparation of a Compound of Formula I, Varying $R^2$

Similarly, following the procedure of 16A above, but replacing (2R,3R,4R,5R)-4-acetyloxy-2-(acetyloxymethyl)-5-[6-(cyclopentylamino)-2-cyanopurin-9-yl]oxolan-3-yl acetate by other compounds of formula (11), the following compounds of Formula I are prepared:

(4S,2R,3R,5R)-5-[2-(2,3,4,5-tetraazolyl)-6-(ethylamino)purin-9-yl]-2-(hydroxymethyl)oxolane-3,4-diol;

(4S,2R,3R,5R)-5-[2-(2,3,4,5-tetraazolyl)-6-(methylamino)purin-9-yl]-2-(hydroxymethyl)oxolane-3,4-diol;

(4S,2R,3R,5R)-5-[2-(2,3,4,5-tetraazolyl)-6-(n-propylamino)purin-9-yl]-2-(hydroxymethyl)oxolane-3,4-diol;

(4S,2R,3R,5R)-5-[6-(bicyclo[2.2.1]hept-2-ylamino)-2-(2,3,4,5-tetraazolyl)purin-9-yl]-2-(hydroxymethyl)oxolane-3,4-diol;

(4S,2R,3R,5R)-5-[6-(benzylamino)-2-(2,3,4,5-tetraazolyl)purin-9-yl]-2-(hydroxymethyl)oxolane-3,4-diol;

(4S,2R,3R,5R)-5-[2-(2,3,4,5-tetraazolyl)-6-(cyclopropylmethylamino)purin-9-yl]-2-(hydroxymethyl)oxolane-3,4-diol;

(4S,2R,3R,5R)-5-[2-(2,3,4,5-tetraazolyl)-6-(cyclopropylamino)purin-9-yl]-2-(hydroxymethyl)oxolane-3,4-diol;

(4S,2R,3R,5R)-5-[2-(2,3,4,5-tetraazolyl)-6-anilinopurin-9-yl]-2-(hydroxymethyl)oxolane-3,4-diol;

(4S,2R,3R,5R)-5-[2-(2,3,4,5-tetraazolyl)-6-(4-chlorobenzylamino)purin-9-yl]-2-(hydroxymethyl)oxolane-3,4-diol;

(4S,2R,3R,5R)-5-[2-(2,3,4,5-tetraazolyl)-6-(2-fluorobenzylamino)purin-9-yl]-2-(hydroxymethyl)oxolane-3,4-diol;

(4S,2R,3R,5R)-5-[2-(2,3,4,5-tetraazolyl)-6-(pyrid-2-ylamino)purin-9-yl]-2-(hydroxymethyl)oxolane-3,4-diol; and (4S,2R,3R,5R)-5-[2-(2,3,4,5-tetraazolyl)-6-(pyrrol-3-ylamino)purin-9-yl]-2-(hydroxymethyl)oxolane-3,4-diol.

D. Preparation of a Compound of Formula I, Varying $R^2$

Similarly, following the procedure of 15A above, but replacing (2R,3R,4R,5R)-4-acetyloxy-2-(acetyloxymethyl)-5-[6-(cyclopentylamino)-2-cyanopurin-9-yl]oxolan-3-yl acetat by other compounds of formula (11), other compounds of Formula I are prepared.

EXAMPLE 17

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 18

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 19

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 20

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 21

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 22

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 23

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 24

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 25

A subcutaneous formulation may be prepared as follows:

| Ingredient | Quantity |
| --- | --- |
| Active Ingredient | 5.0 mg |
| Corn Oil | 1.0 mL |

EXAMPLE 26

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

EXAMPLE 27

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 28

| Sustained Release Composition | | | |
| --- | --- | --- | --- |
| Ingredient | Weight Range (%) | Preferred Range (%) | Most Preferred |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, for example sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets for example have a hardness sufficient to withstand 8 Kp compression. The tablet size will depend primarily upon the amount of compound in the tablet. The tablets will include from 300 to 1100 mg of compound free base. For example, the tablets will include amounts of compound free base ranging from 400-600 mg, 650-850 mg, and 900-1100 mg.

In order to influence the dissolution rate, the time during which the compound containing powder is wet mixed is controlled. For example the total powder mix time, i.e. the time during which the powder is exposed to sodium hydroxide solution, will range from 1 to 10 minutes and for example from 2 to 5 minutes. Following granulation, the particles are removed from the granulator and placed in a fluid bed dryer for drying at about 60° C.

EXAMPLE 29

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 µg $mL^{-1}$ amphotericin B, 100 U $mL^{-1}$ penicillin G, 0.1 mg $mL^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 mL), scraped free of the plate with the aid of a rubber policeman in 5 mL of 50 mM Tris-HCl buffer pH 7.4 at 4° C. and the suspension was homogenized for 10 s. The suspension was then centrifuged at 27,000×g for 10 min. The pellet was resuspended in homogenization buffer by vortexing and centrifuged again as described above. The final pellet was resuspended in 1 vol of 50 mM Tris-HCl buffer pH 7.4 containing 5 mM $MgCl_2$ for $A_1$ adenosine receptor assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min and stored at −80° C. Aliquots of the membrane suspension were later thawed and used for assays. The protein content was determined with a BradfordTm Assay Kit using bovine serum albumin as standard.

Competitive Binding Assay

Compounds of Formula I were assayed by use of competitive radioligand binding methods to determine their affinity for the $A_1$ adenosine receptor sites on the membranes of DDT cells. Briefly, 50-70 ug of membrane protein were incubated in a mixture containing 2U/ml adenosine deaminase and 10 µM GTP-γS in 50 mM Tris-HCl buffer, pH 7.4, with 1 mM EDTA in glass tubes Stock solutions of the compounds of the invention were serially diluted ($10^{-10}$M to $10^{-4}$M) in Tris buffer and added to the incubation mixture. Finally, tritiated 8-cyclopentyl-1,1-dipropylxanthine ($^3$H-CPA) was added to a final concentration of 1.5 nM. After incubation at 23° C. 90 minutes, the reaction was stopped by filtration on a Brandel MR24 cell harvester and washing with ice-cold Tris-EDTA buffer (three times, approximate volume 10 ml/wash) over Whatman GF/B filters (presoaked for 1 h in 0.3% polyethylenimine to reduce non-specific binding). Filters were transferred to scintillation vials and 5 ml of Scintisafe (VWR, Brisbane, Calif.) was added. The amount of radioactivity retained on the filters was determined by liquid scintillation spectrometry. Protein determinations were by the method of Bradford (1976. *Anal. Biochem.* 72:248) using bovine serum albumin as the standard.

The compounds of Formula I were shown to be of high, medium, or low affinity for the $A_1$ adenosine receptor in this assay. The $K_i$ values for several of the compounds of the invention are presented in Table 1 below.

TABLE 1

| | $A_1$ BINDING AFFINITY | |
|---|---|---|
| COMPOUND NO. | NAME | $K_i$ nM |
| I. | (4S,3R,5R)-2-[6-(cyclopentylamino)-2-(1,2,3,4-tetraazolyl)purin-9-yl]-5-(hydroxymethyl)oxolane-3,4-diol; | 1 |
| II. | ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate; | 3 |
| III. | (1-{9-[(4S,3R,5R)-3,4-dihydroxy-5-(hydroxymethyl)oxolan-2-yl]-6-(cyclopentylamino)purin-2-yl}(1,2,3-triazol-4-yl))-N-methylcarboxamide; | 2 |
| IV. | 1-{9-[(4S,3R,5R)-3,4-dihydroxy-5-(hydroxymethyl)oxolan-2-yl]-6-(cyclopentylamino)purin-2-yl}-1,2,3-triazole-4-carboxamide; | 16 |
| V. | (4S,2R,3R,5R)-2-[6-(cyclopentylamino)-2-(1,2,3,4-tetraazolyl)purin-9-yl]-5-(hydroxymethyl)oxolane-3,4-diol | 8.25 |

EXAMPLE 30

[$^{35}$S]GTPγS Binding Assays $A_1$ adenosine receptor agonist stimulated [$^{35}$S]GTPγS binding was determined by a modification of the method described by Giersckik et al. (1991) and Lorenzen et al. (1993). Membrane protein (30-50 µg) was incubated in a volume of 0.1 mL containing 50 mM Tris-HCl buffer pH 7.4, 5 mM $MgCl_2$, 100 mM NaCl, 1 mM dithiothreitol, 0.2 units $mL^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 µM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 µM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5-1000 nM GTPγS. At the end of the incubation, each suspension was filtered and the retained radioactivity determined as described above.

The compounds of Formula I were shown to be partial or full agonists of the $A_1$ adenosine receptor in this assay.

EXAMPLE 31 cAMP Assay

A scintillation proximity assay (SPA) using rabbit antibodies directed at cAMP and an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 µl of HBSS at 37° C.

(5% CO$_2$ and 95% humidity). The partial or full A$_1$ agonists (5 μl) of this invention were incubated at various concentrations with the DDT$_1$ cells in the presence of rolipram (50 μM), and 5 μM forskolin for 10 min at 37° C. The cells were immediately lysed by treatment with 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) was added to each well followed by sealing the plate. After 15-20 h at 23° C., the amount of bound [$^{125}$I] cAMP to the fluoromicrospheres was determined by counting in a microtitre plate scintillation counter for 2 minutes. Comparison of counts with standard curves generated for cAMP using a similar protocol afforded the cAMP present after cell lysis.

The compounds of Formula I were shown to be functionally active as A$_1$ agonists with a partial or full decrease in cAMP in this assay.

What is claimed is:

1. A compound having the structure of Formula I:

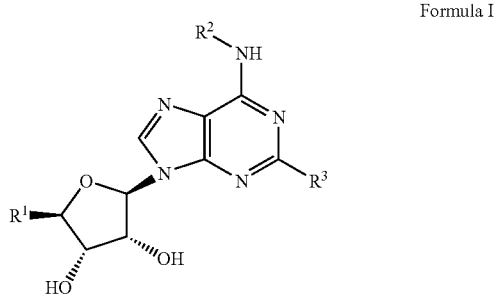

Formula I wherein:

R$^1$ is hydroxymethyl;

R$^2$ is benzyl, five or six membered monocyclic cycloalkyl or five or six membered monocyclic heterocyclyl; and R$^3$ is selected from

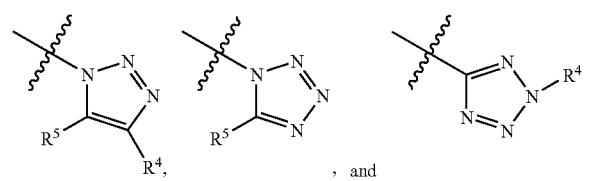

, and wherein R$^4$ and R$^5$ are independently selected from hydrogen; C$_{1-6}$ alkyl, C$_{2-6}$ alkenyl, or C$_{2-6}$ alkynyl optionally substituted with hydroxy, alkoxy, or five or six membered monocyclic aryl; five or six membered monocyclic aryl optionally substituted with halo, hydroxy, alkoxy, or CF$_3$; —CO$_2$H; —SO$_3$H; —C(O)OR$^6$; CH(OH)R$^6$; or C(O)NR$^6$R$^7$;

wherein R$^6$ and R$^7$ are hydrogen, alkyl optionally substituted with hydroxy, alkoxy, or aryl; five or six membered monocyclic cycloalkyl, or five or six membered monocyclic.

2. The compound of claim 1, wherein R$^3$ is:

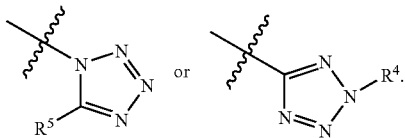

or

3. The compound of claim 1, wherein R$^3$ is:

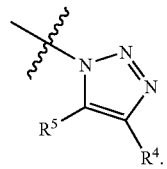

4. The compound of claim 1, wherein R$^2$ is a five or six membered monocyclic heterocyclyl.

5. The compound of claim 3, wherein R$^2$ is a five membered heterocyclic ring having at least one nitrogen or oxygen atom.

6. The compound of claim 4, wherein at least one of R$^4$ and R$^5$ are hydrogen.

7. The compound of claim 5, wherein R$^4$ is optionally substituted aryl.

8. The compound of claim 1, namely 2-(6-[((3R)oxolan-3-yl)amino]-2-{4-[4-(trifluoromethyl)phenyl](1,2,3-triazolyl)}purin-9-yl)-5-(hydroxymethyl)oxolane-3,4-diol.

9. The compound of claim 5, wherein R$^4$ is —CO$_2$H, —SO$_3$H, —C(O)OR$^6$, —CH(OH)R$^6$, or C(O)NR$^6$R$^7$.

10. The compound of claim 1, namely ethyl 1-{6-[((3R)oxolan-3-yl)amino]-9-[3,4-dihydroxy-5-(hydroxymethyl)oxolan-2-yl]purin-2-yl}-1,2,3-triazole-4-carboxylate.

11. The compound of claim 5, wherein R$^4$ is hydrogen or alkyl optionally substituted with hydroxy, alkoxy, or five or six membered monocyclic aryl.

12. The compound of claim 1, namely 2-{6-[((3R)oxolan-3-yl)amino]-2-[4-(hydroxymethyl)(1,2,3-triazolyl)]purin-9-yl}-5-(hydroxymethyl)oxolane-3,4-diol.

13. The compound of claim 2, wherein R$^2$ is an cycloalkyl moiety.

14. The compound of claim 12, wherein at least one of R$^4$ and R$^5$ are hydrogen.

15. The compound of claim 13, wherein R$^4$ is —CO$_2$H, —SO$_3$H, —C(O)OR$^6$, —CH(OH)R$^6$, or C(O)NR$^6$R$^7$.

16. The compound of claim 1, selected from the group consisting of:

ethyl 1-{9-[(4S,3R,5R)-3,4-dihydroxy-5-(hydroxymethyl)oxolan-2-yl]-6-(cyclopentylamino)purin-2-yl}-1,2,3-triazole-4-carboxylate;

(1-{9-[(4S,3R,5R)-3,4-dihydroxy-5-(hydroxymethyl)oxolan-2-yl]-6-(cyclopentylamino)purin-2-yl}(1,2,3-triazol-4-yl))-N-methylcarboxamide;

1-{9-[(4S,3R,5R)-3,4-dihydroxy-5-(hydroxymethyl)oxolan-2-yl]-6-(cyclopentylamino)purin-2-yl}-1,2,3-triazole-4-carboxamide;

1-{9-[(4S,3R,5R)-3,4-dihydroxy-5-(hydroxymethyl)oxolan-2-yl]-6-(cyclopentylamino)purin-2-yl}-1,2,3-triazole-4-carboxylic acid; and ethyl 1-{9-[(4S,3R,5R)-3,4-dihydroxy-5-(hydroxymethyl)oxolan-2-yl]-6-(cyclohexylamino)purin-2-yl}-1,2,3-triazole-4-carboxylate.

17. The compound of claim 13, wherein $R^4$ is hydrogen or alkyl, alkenyl, or alkynyl optionally substituted with hydroxy, alkoxy, or five or six membered monocyclic aryl.

18. The compound of claim 1, selected from the group consisting of:
- (4S,3R,5R)-2-{6-(cyclopentylamino)-2-[4-benzyl(1,2,3-triazolyl)]purin-9-yl}-5-(hydroxymethyl)oxolane-3,4-diol;
- [(1-{9-[(4S,3R,5R)-3,4-dihydroxy-5-(hydroxymethyl)oxolan-2-yl]-6-(cyclopentylamino)purin-2-yl}(1,2,3-triazol-4-yl))methyl][(4-fluorophenyl)sulfonyl]amine;
- [(1-{9-[(4S,3R,5R)-3,4-dihydroxy-5-(hydroxymethyl)oxolan-2-yl]-6-(cyclopentylamino)purin-2-yl}(1,2,3-triazol-5-yl))methyl][(4-fluorophenyl)sulfonyl]amine; and
- (4S,3R,5R)-2-[6-(cyclopentylamino)-2-(1,2,3,4-tetraazolyl)purin-9-yl]-5-(hydroxymethyl)oxolane-3,4-diol.

19. The compound of claim 1, wherein $R^2$ is an optionally substituted aryl or benzyl.

20. A method for treating a disease or condition selected from atrial fibrillation, atrial flutter, congestive heart failure, stroke, epilepsy, diabetes, ischemia, stable angina, unstable angina, myocardial infarction, cardiac transplant, hyperlipidemia and hypertriglyceridemia comprising the administration to a mammal in need thereof of an amount of compound of claim 1 that is therapeutically effective to fully or partially agonize an Adenosine $A_1$ receptor.

21. The method of claim 20, wherein the mammal is human.

22. A pharmaceutical composition comprising at least one pharmaceutically acceptable excipient and a therapeutically effective amount of a compound of claim 1.

* * * * *